United States Patent
Liu

(10) Patent No.: US 8,017,332 B2
(45) Date of Patent: Sep. 13, 2011

(54) MAGNETIC METHOD FOR RECOVERING NUCLEIC ACID FROM A MIXED CELL SUSPENSION

(75) Inventor: Yingjie Liu, Foster City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 374 days.

(21) Appl. No.: 12/032,270

(22) Filed: Feb. 15, 2008

(65) Prior Publication Data

US 2008/0206771 A1    Aug. 28, 2008

Related U.S. Application Data

(60) Provisional application No. 60/890,460, filed on Feb. 16, 2007.

(51) Int. Cl.
   C12Q 1/68    (2006.01)
   C12P 19/34   (2006.01)
   C12N 13/00   (2006.01)

(52) U.S. Cl. ....... 435/6.1; 435/6.12; 435/91.2; 536/25.4

(58) Field of Classification Search ............. 435/6, 91.2; 536/25.4

See application file for complete search history.

(56) References Cited

U.S. PATENT DOCUMENTS

| | | | |
|---|---|---|---|
| 5,234,809 A |  | 8/1993 | Boom |
| 5,523,231 A |  | 6/1996 | Reeve |
| 5,705,628 A |  | 1/1998 | Hawkins |
| 6,855,499 B1 | * | 2/2005 | Nargessi .......................... 435/6 |
| 2002/0151089 A1 |  | 10/2002 | Chapman, Jr. et al. |
| 2003/0215845 A1 |  | 11/2003 | Bille |
| 2005/0064575 A1 | * | 3/2005 | Belgrader et al. ............ 435/259 |
| 2006/0141512 A1 |  | 6/2006 | Sinha et al. |
| 2008/0176320 A1 |  | 7/2008 | Liu |
| 2008/0261293 A1 |  | 10/2008 | Garvin |

FOREIGN PATENT DOCUMENTS

| | | |
|---|---|---|
| WO | WO01/35759 A1 | 5/2001 |
| WO | WO 01/52968 A1 * | 7/2001 |

OTHER PUBLICATIONS

PCT International Search Report, Authorized Officer Kenneth R. Horlick, Jul. 3, 2008, 3 pages.
Office Action for U.S. Appl. No. 12/015,414, mailed Nov. 26, 2010.
Chen et al. "A physical method for separating spermatozoa from epithelial cells in sexual assault evidence", Journal of Forensic Science, 43:114-118 (1998).
Gill et al. "Forensic Application of DNA Fingerprints", Nature 318:577-579 (1985).
Westbrook et al. "Differential nuclear localization of the cancer/testis-associated protein, SPAN-X/CTp11, in transfected cells and in 50% of human spermatozoa", Biology of Reproduction 64:345-358 (2001).
International Preliminary Report on Patentability, mailed Aug. 27, 2009, for PCT/US2008/054132.

* cited by examiner

*Primary Examiner* — Kenneth R. Horlick
(74) *Attorney, Agent, or Firm* — Shirley A. Recipon

(57) ABSTRACT

A method for selectively recovering nucleic acid from a first cell type in a sample containing cells of at least a first cell type and a second cell type, and a cell suspension medium comprising extracellular impurities, is provided. The method entails combining the sample with particles responsive to a magnetic field in a vessel, the magnetic particles having the ability to sequester the cells from the cell suspension medium upon application of a magnetic field; exposing the vessel to a magnetic field for a time sufficient to cause sequestration of the cells by the particles; removing the impurities-containing cell suspension medium from the vessel while retaining the cells; lysing selectively cells of the first cell type; and isolating the nucleic acid from the lysed cells. Methods for recovering nucleic acid from the second cell type are also provided.

22 Claims, 15 Drawing Sheets

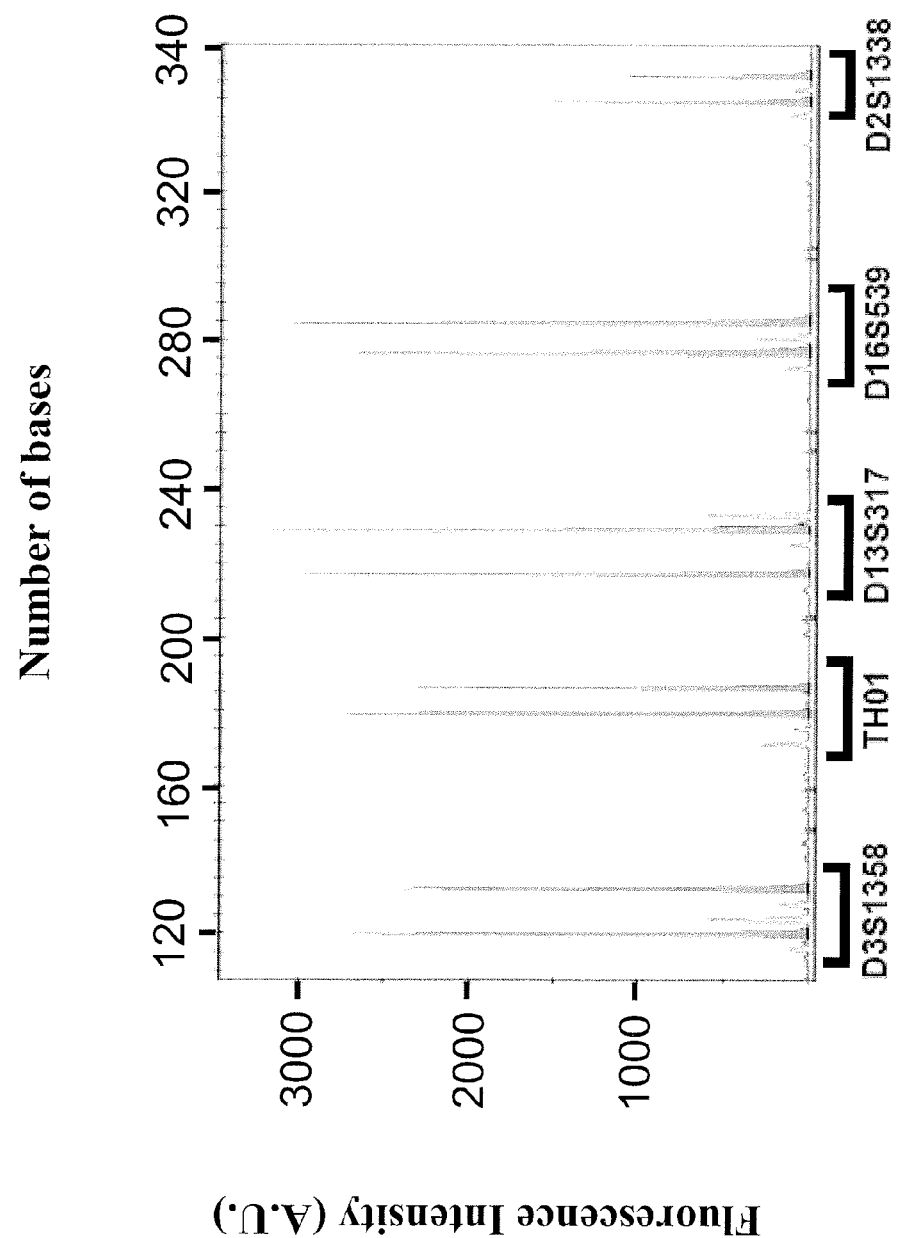

MAGNETIC METHOD FOR RECOVERING NUCLEIC ACID FROM A MIXED CELL SUSPENSION

CROSS REFERENCE TO RELATED APPLICATIONS

This application claims priority benefit under 35 U.S.C. §119(e) from U.S. Application No. 60/890,460 filed Feb. 16, 2007, the contents of which are incorporated herein by reference.

FIELD OF THE INVENTION

The invention relates to the field of isolating cells from a sample containing cells and non-cell impurities and further isolating nucleic acid from a specific cell type.

More specifically, the invention relates to the field of isolating sperm cells from a sample containing extracellular impurities and at least one other type of contaminating cell (e.g., epithelial cells) and recovering DNA from the sperm cells and nonsperm cells for various purposes, including forensic purposes.

BACKGROUND OF THE INVENTION

Forensic DNA analysis of sexual assault evidence often involves analysis of DNA from sperm cells and DNA from other cells such as epithelial cells. Sperm cells are normally obtained from a rape victim by rubbing a swab against a mucous membrane. The samples obtained from victims often contain a mixture of sperm and epithelial cells. Because the epithelial cells may outnumber sperm cells in the sample by at least an order of magnitude, the former can cause contamination of sperm cell DNA, when sperm DNA is purified. Therefore, it is often desirable to separate, as cleanly as possible, the sperm cells and epithelial cells, or the sperm DNA and the epithelial DNA, prior to analysis. Separation and isolation of DNA from sperm and epithelial cells are essential steps in identifying an assailant from a forensic specimen, and in associating the assailant with the victim.

The standard method for purifying sperm from swabs is based on differential extraction. Separation of the sperm DNA from the victim's DNA removes ambiguity, facilitates DNA analysis and allows for easier interpretation of the assailant's DNA profile in a rape case. Although differential extraction is commonly used to separate sperm and epithelial cells, the standard protocol is time consuming and laborious.

Typically, cells are first resuspended from a forensic specimen, followed by selective digestion of the victim's epithelial cells with a solution containing Proteinase K and SDS (sodium dodecyl sulfate). The intact sperm are separated from the solubilized, contaminating DNA and epithelial cell debris by centrifugation, careful removal of supernatant, and extensive washing of the sperm pellet (see e.g., Giusti et al., J. Forensic Sci., 31:409-417, 1986; Gill et al. *Nature* 318:577-579, 1985; Wiegand et al., Int J. Legal Med., 104:359-360, 1992; and Yoshida et al., Forensic Sci. Int., 72:25-33, 1995). Unfortunately, the processes of centrifugation and careful removal of supernatant are difficult to automate and can cause the loss of sperm DNA due to multiple sample handling steps.

In one example of this procedure, Gill et al. (supra) describe a process for isolating sperm DNA from vaginal swabs taken from sexual assault victims. These swabs contain sperm and also a large excess of the victim's epithelial cells. The epithelial cells and the DNA contained in these cells is removed by preferential lysis (i.e., by incubation of the cell mixture in a buffer solution containing SDS, and proteinase K). Sperm nuclei are impervious to this treatment because they have disulfide bond cross-linked thiol-rich proteins, while other cell types are digested and the corresponding DNA is solubilized. After preferential lysis, the samples are centrifuged to separate the sperm nuclei from the victim's solubilized DNA. The supernatant containing the victim's DNA is removed and the sperm pellet is washed repeatedly. The sperm nuclei are subsequently lysed by treatment with a buffer solution containing SDS, proteinase K and DTT (dithiothreitol), and the lysate separated from the contaminating cells by centrifugation.

Wiegand et al. (supra) attempted to improve on the method of Gill et al. for samples having low sperm counts by using mild lysis conditions and by avoiding the washing steps.

A number of proposals for separating sperm cells from epithelial steps are based on filtration. Thus, Chen et al. (J Forensic Science 43:114-118, 1998) and Garvin (PCT/US01/01835) separate the sperm from the epithelial cells before differential lysis by gravitational or mild vacuum filtration or by use of a filter material that can withstand strong vacuum or centrifugal forces without having the pores increase in size. DNA is then isolated from the sperm collected in the filtrate.

A drawback of centrifugation-based methods is that centrifugation is difficult to automate. In addition, because of the loose nature of the cell pellets, the separation of supernatant containing DNA from the cell pellets is incomplete and causes cross-contamination between sperm cell and epithelial cell fractions. Centrifugation and vacuum steps can also damage the integrity of intact cells because of the harshness of the processes, thereby further reducing the likelihood of accurate results.

Attempts have also been made to use anti-sperm antibody coated magnetic beads (Eisenberg, A. J. "Development of a Spermatozoa Capture System for the Differential Extraction of Sexual Assault Evidence"; paper presented at: Profiling PCR and Beyond Conference, 2002; Washington, D.C.). Epitope stability, however, is a problem with this approach when applied to forensic work, because detergents such as Sarkosyl or SDS are required to efficiently elute sperm from the swabs and these detergents compromise epitopes recognized by the anti-sperm antibodies, reducing the number of sperm cells that can be separated and recovered.

In general, antibody-coated magnetic beads have been successfully used for many cell separation applications (Haukanes & Kvam, Biotechnology (NY). 11:60-63, 1993), but they have not been used to simply sequester cells in a process wherein DNA isolation is ultimately sought. Additional impediments may be present because human cells in forensic specimens have been dried onto an adsorbent substrate and then resuspended. In addition, because sperm lysis buffer can alter epitopes recognized by the anti-sperm antibodies, new antibodies recognizing different epitopes would most likely have to be employed, if sperm cell extraction is to be carried out with immuno-molecules.

Because of the difficulties of purifying sperm with immuno-molecules, size exclusion filters, such as the ones employed by Garvin and Chen (supra), have been employed.

SUMMARY OF THE INVENTION

The present invention serves as an alternative to centrifugation, vacuum, size exclusion filtration and immuno-separation, for the isolation of sperm cells, and sperm cell DNA, present in a heterogeneous sample of cells, which in a particular forensic application include epithelial cells. It is readily adaptable to automation and high throughput with existing equipment such as the Beckman Biomek® (Beckman Coulter, Fullerton, Calif.) or a Tecan liquid automated handling system (e.g., Freedom Evo® services Tecan Systems, San Jose, Calif.). The invention is more widely applicable to both forensic and other situations where nucleic acid has to be isolated from one type of cell found in a mixture of more than one type of cell, as long as each cell type can be selectively lysed (except the last remaining cell type which need not be selectively lysed).

The present invention, in one aspect, is directed to a method for selectively recovering nucleic acid from a first cell type in a sample containing cells of at least the first cell type and a second cell type, and a cell suspension medium comprising extracellular impurities. The method entails combining the sample with particles responsive to a magnetic field in a vessel, the magnetic particles having the ability to sequester the cells from the cell suspension medium or other supernatant upon application of a magnetic field; applying a magnetic field to the vessel, thereby causing sequestration of intact cells in the suspension by the particles; removing the impurities-containing supernatant from the vessel while retaining the cells; lysing selectively cells of the first cell type; and isolating the nucleic acid from the lysed cells.

It is to be understood that in certain embodiments the foregoing selective lysis of cells of the first type can precede the sequestration step. For example, in various forensic applications involving isolating sperm DNA from epithelial cell DNA, the epithelial cells can first be selectively lysed and then the magnetic field can be applied to sequester the intact cells left in the suspension, i.e., the sperm cells, from the suspension medium which will then also include the lysate of the epithelial cells.

In a particular aspect of the invention, the sample comprises a forensic specimen, which can include a specimen taken from a sexual assault victim. The cell types in such a sample are sperm and epithelial cells. In principle, the nucleic acid in a sample can be DNA or mRNA or total RNA.

Selective lysis of the first cell type may be carried out by discontinuing application of the magnetic field and exposing the sequestered cells to a selective lysis buffer and for a period time sufficient to lyse the cells of the first type.

In another aspect, the present invention is directed to a method for identifying a nucleic acid from a first cell type in a sample containing cells of at least the first cell type and a second cell types and a supernatant comprising extracellular impurities. The method entails combining the sample with particles responsive to a magnetic field in a vessel, the magnetic particles having the ability to sequester the cells from the supernatant upon application of a magnetic field; applying a magnetic field to the vessel, thereby causing sequestration of the cells by the particles; removing the impurities-containing supernatant from the vessel while retaining the cells; lysing selectively cells of the first cell type; isolating and purifying the nucleic acid from the lysed cells. Further downstream steps typically include quantifying the purified nucleic acid as well as amplifying and separating the amplified short tandem repeats fragments for genotyping.

Another aspect of the invention is directed to a kit for the isolation and recovery of nucleic acid from a first cell type in a sample containing cells of at least the first cell type and a second cell type, and a cell suspension medium comprising extracellular impurities. The kit includes a predetermined quantity of particles responsive to a magnetic field adapted and sufficient to sequester the cells from the cell suspension medium, upon use of said kit; at least one vessel for carrying out lysis and separation steps; a predetermined quantity of selective lysis buffer for the first cell type, said quantity being sufficient to lyse cells of the first cell type in the sample; a predetermined quantity of lysis buffer for the second cell type, said quantity being sufficient to lyse cells of the second type in the sample, reagents for nucleic acid purification and instructions for performing the isolation and recovery of said nucleic acid.

BRIEF DESCRIPTION OF THE DRAWINGS

The skilled artisan will understand that the drawings, described below, are for illustration purposes only. The drawings are not intended to limit the scope of the present teachings in any way.

FIG. 2A-2D are STR typing profiles of sperm DNA isolated with the method of the invention as illustrated in Example 1. The sperm cells were originally in a sample containing extraneous E-cell DNA, sperms and E-cells. Primers for the various loci were labeled with a fluorescent dye, followed by amplification of the various loci and separation of products by electrophoresis. Fluorescence excitation/emission wavelengths and dyes employed were 494/522 nm, 6-FAM (FIG. 2A), 538/554 nm, VIC (FIG. 2B), 546/575 nm, NED (FIG. 2C), 558/595 nm, PET (FIG. 2D). The loci names are listed below the corresponding peaks.

DETAILED DESCRIPTION OF CERTAIN EMBODIMENTS OF THE INVENTION

Definitions

Figure 1:
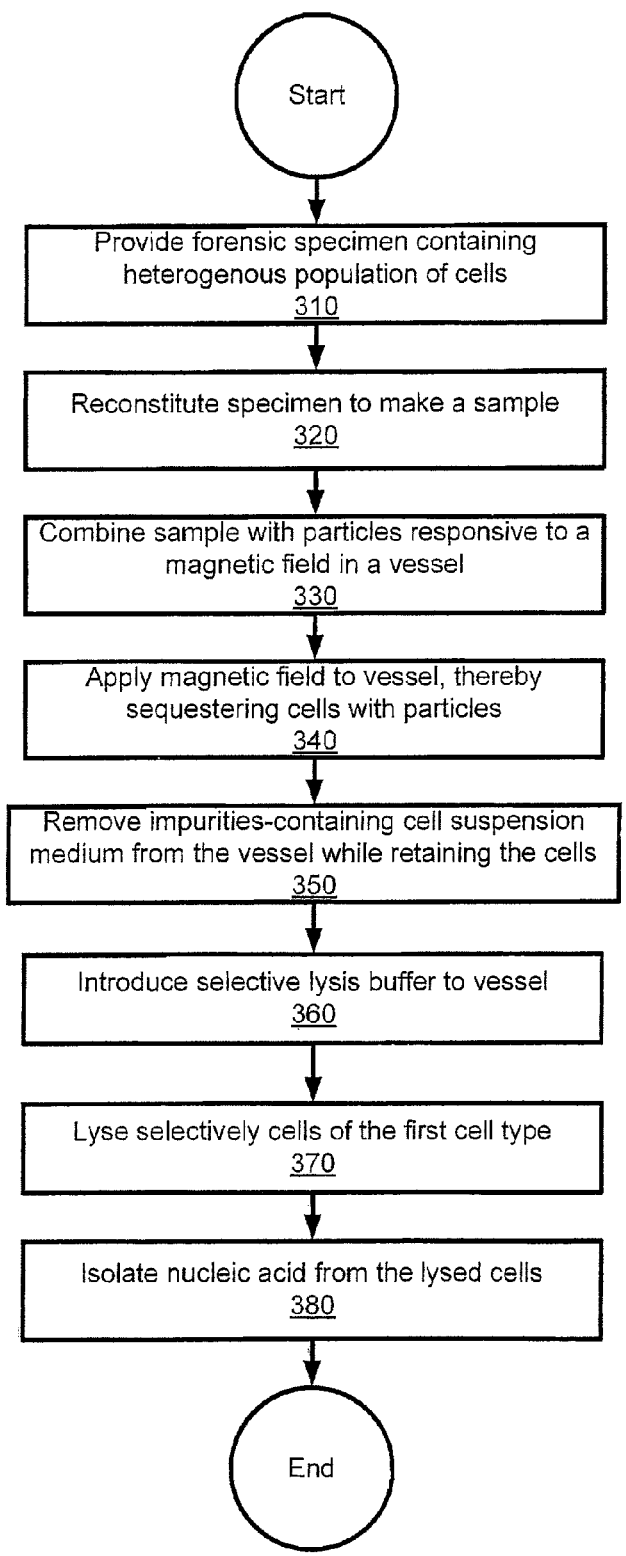
FIG. 1 is a process flow chart showing steps to isolate and recover DNA from multiple cell types, in accordance with one particular embodiment of the present invention.
Figure 2A:
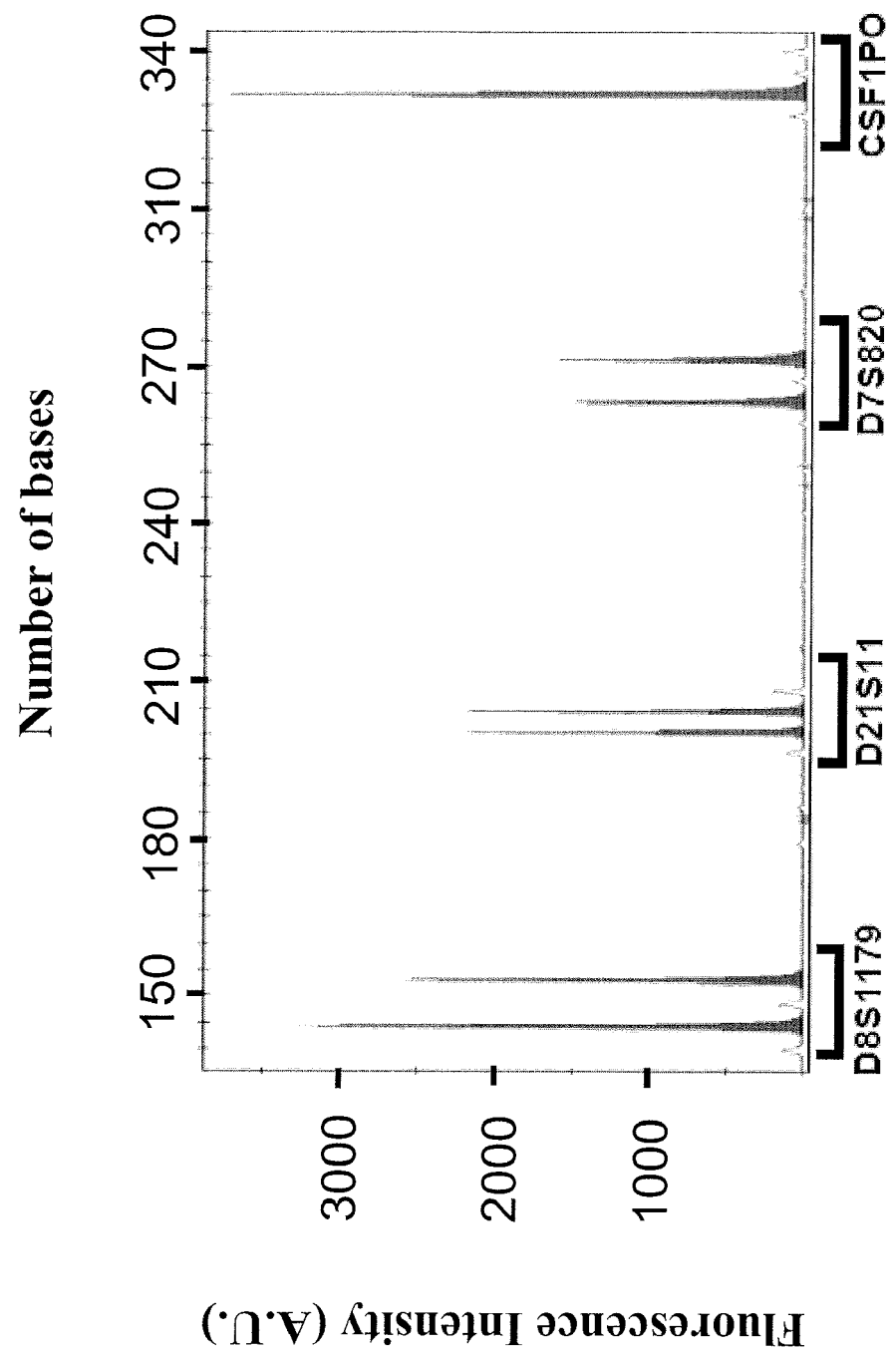
Figure 2C:
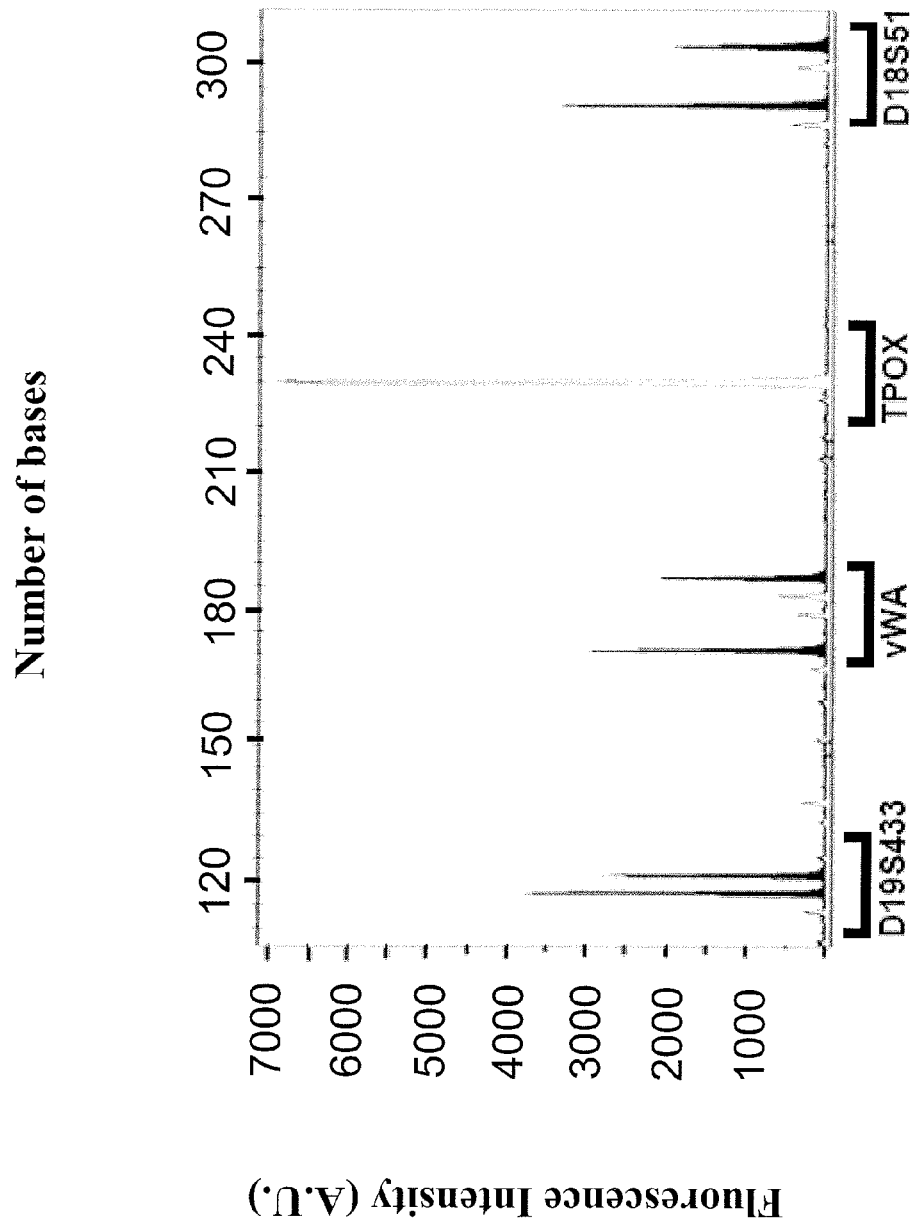
Figure 2D:
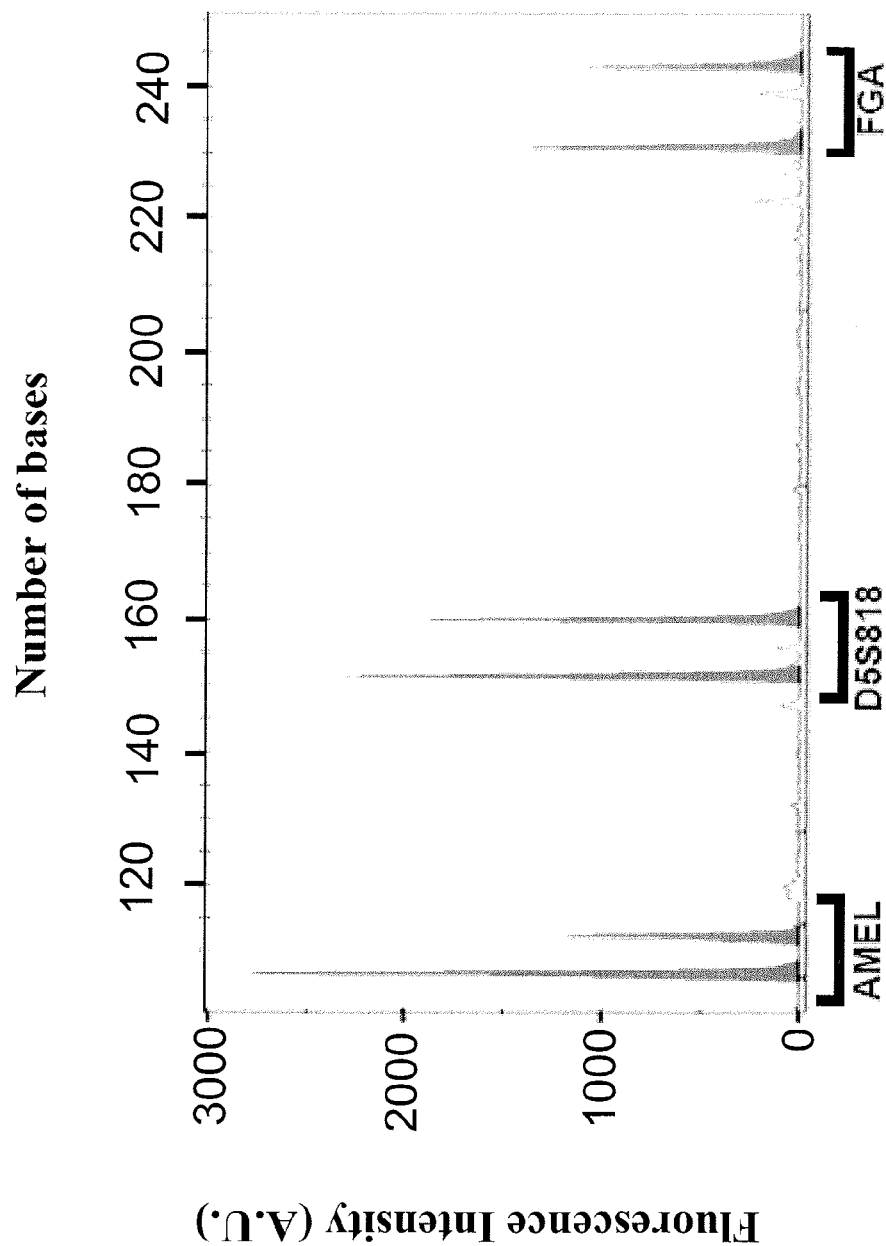
Figure 2E:
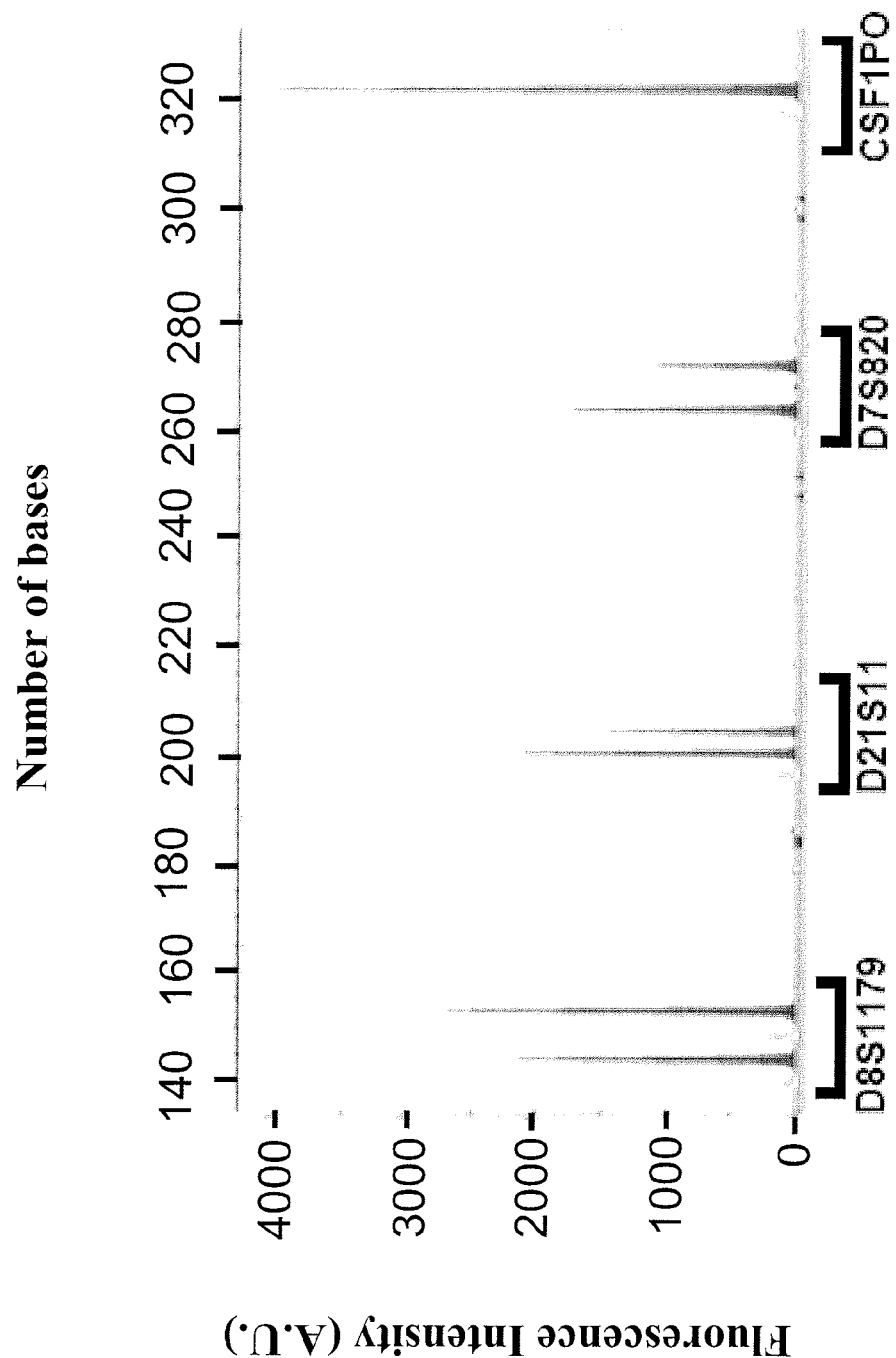
FIG. 2E-2H are STR typing profiles of purified control sperm DNA, run for comparison with FIGS. 2A-2D. Primers for the various loci were labeled with a fluorescent dye, followed by amplification of the various loci and separation of products by electrophoresis. Fluorescence excitation/emission wavelengths and dyes employed were 494/522 nm, 6-FAM (FIG. 2E), 538/554 nm, VIC (FIG. 2F), 546/575 nm, NED (FIG. 2G), 558/595 nm, PET (FIG. 2H). The loci names are listed below the corresponding peaks.
Figure 2F:
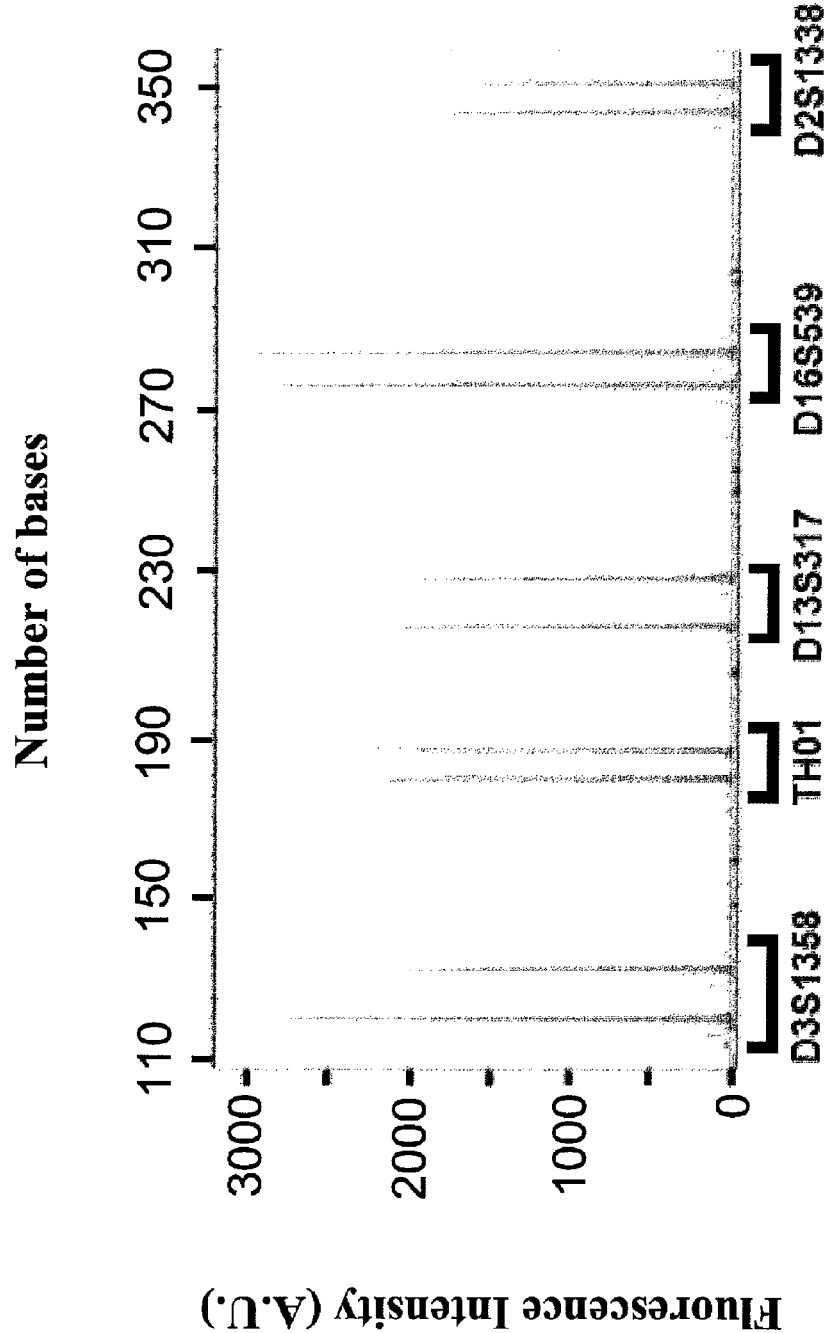
Figure 2G:
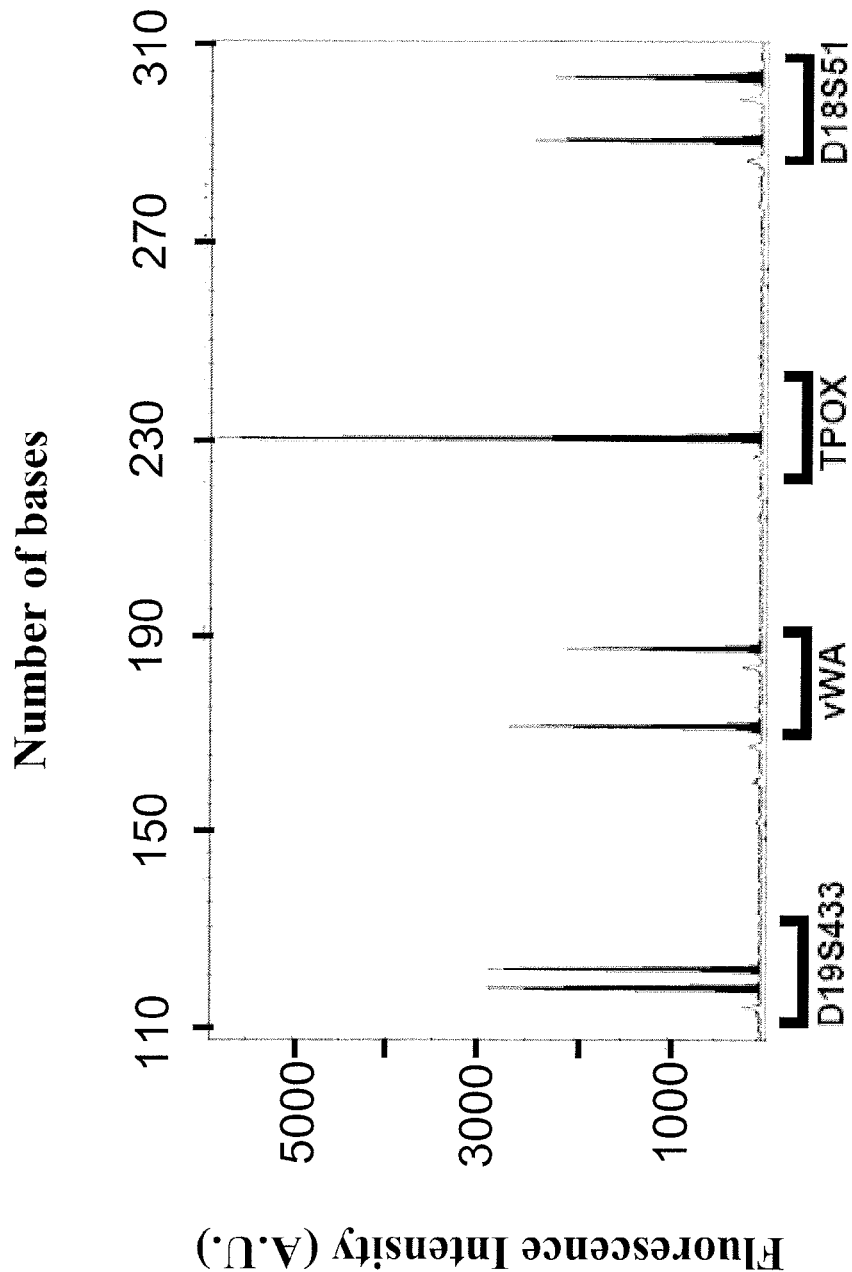
Figure 2H:
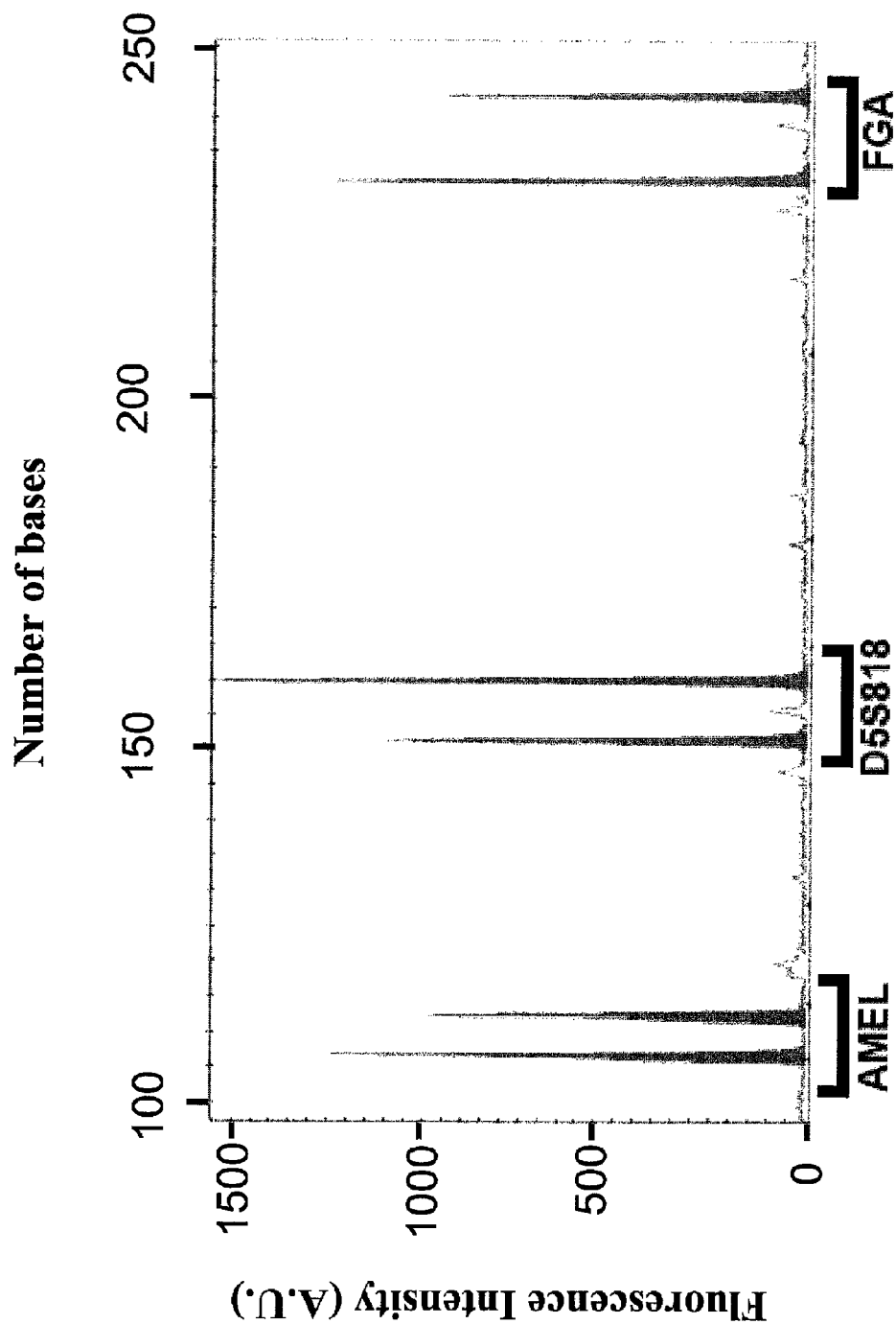
Figure 3A:
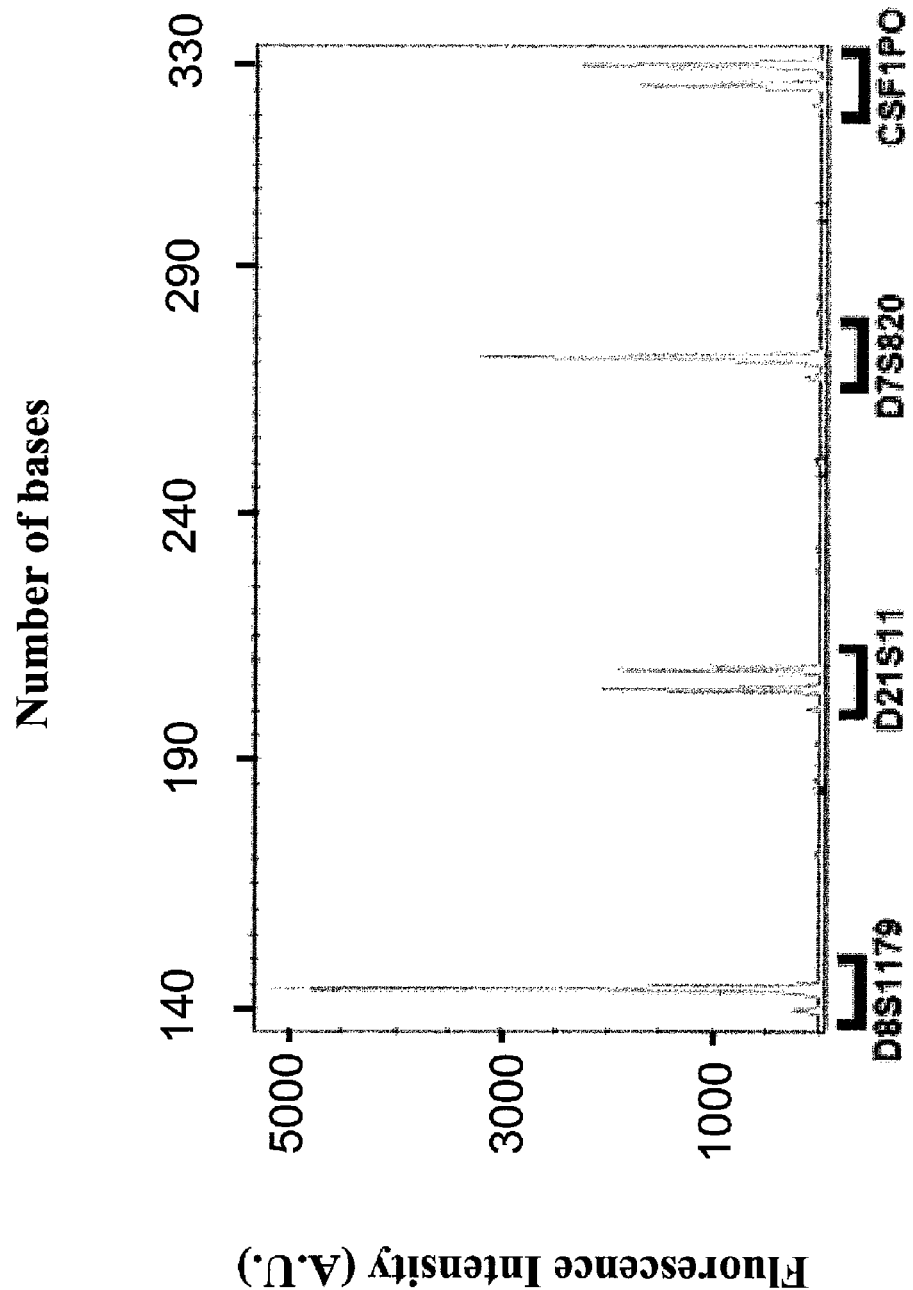
FIG. 3A-3D are results showing the purity of epithelial DNA, isolated from a sample containing extraneous E-cell DNA, sperms and E-cells as illustrated in Example 1. Sperm DNA was isolated first. Primers for the various loci were labeled with a fluorescent dye, followed by amplification of the various loci. Fluorescence excitation/emission wavelengths and dyes employed were 494/522 nm, 6-FAM (FIG. 3A), 538/554 nm, VIC (FIG. 3B), 546/575 nm, NED (FIG. 3C), 558/595 nm, PET (FIG. 3D). The loci names are listed below the corresponding peaks.
Figure 3B:
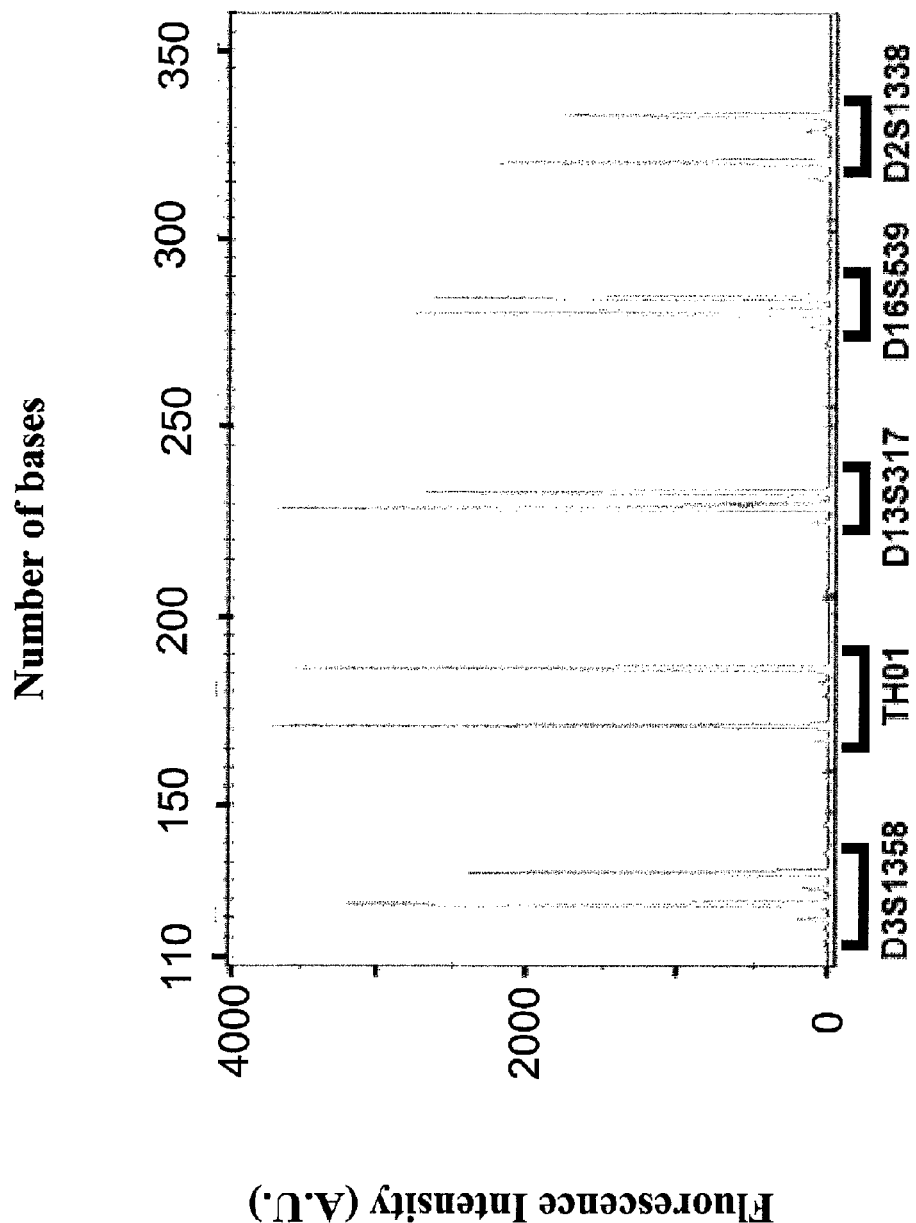
Figure 3C:
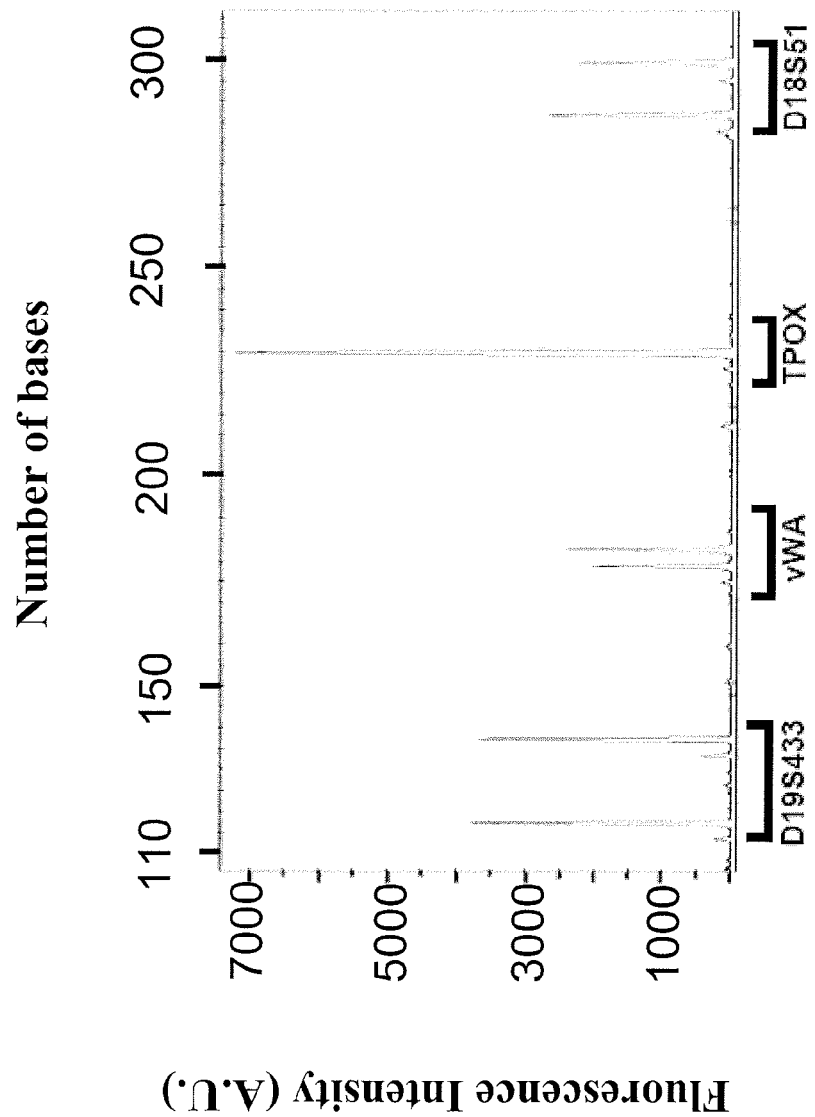
Figure 3D:
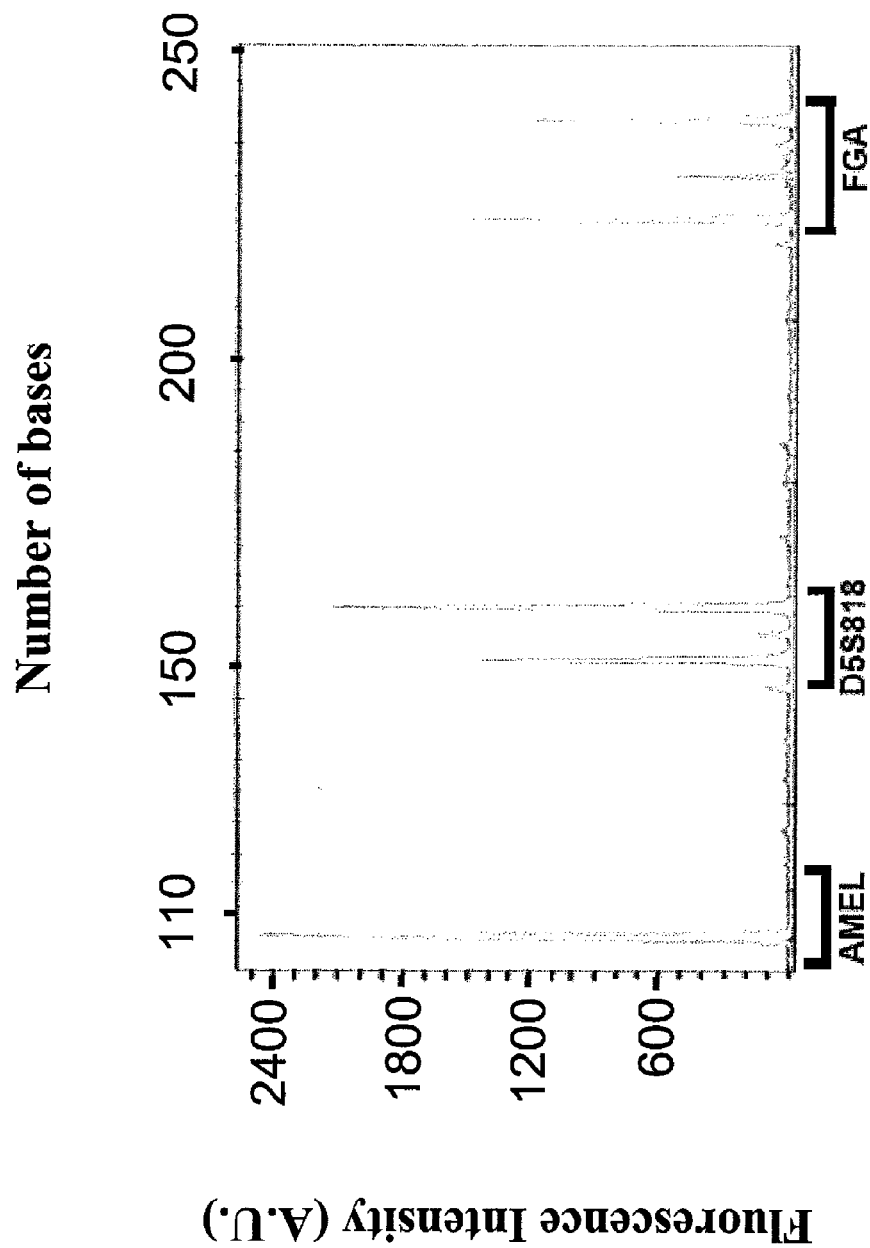

The term "nucleic acid" as used herein, encompasses both DNA and RNA molecules, as well as DNA/RNA chimeras and nucleic acid molecules with unnatural bases and/or sugar moieties. In a particular forensic embodiment, DNA from sperm cells of the assailant is isolated from DNA of nonsperm cells (usually epithelial cells) of the victim.

The "sample" used in the present invention can be any heterogeneous cellular suspension containing two or more cell types wherein at least one of the types of cells can be selectively lysed. The sample also includes suspension medium such as reconstituting buffer which also contains impurities from the sample, e.g., extraneous DNA. In some embodiments, the sample is reconstituted from a forensic specimen.

The term "forensic specimen", as used herein, means a specimen obtained to address legal issues, including, but not limited to, murder, rape, trauma, assault, battery, theft, burglary, other criminal matters, identity, paternity testing, and mixed application samples. It broadly refers to a substrate which contains a specimen of biological materials such as blood, blood stains, saliva, skin debris, feces, feces stains, urine, sperm cells, epithelial cells, muscle tissue, bone or muscle remains, or mummified remains. In some embodiments, the "forensic specimen" is contained on, and includes, a swab or cotton applicator on which the biological specimen is collected.

The term "differential extraction", as used herein, refers to extraction methods used to separate nucleic acid from individual cell types within a heterogeneous population of cells, for example, such as the selective lysis of sperm cells in an epithelial-sperm cell mixture.

The two or more "cell types" amenable for use in embodiments of the present invention can include any two or more of the following, as long as at least one cell type, in the mixture can be selectively lysed: sperm cells, epithelial cells, erythrocytes, platelets, neutrophils, lymphocytes, monocytes, eosinophils, basophils, adipocytes, chrondrocytes, tumor cells, neurons, glial cells, astrocytes, red blood cells, white blood cells, macrophages, hair cells, bladder cells, kidney cells, retinal cells, rod cells, cone cells, antigen presenting cells, T-cells, B-cells, plasma cells, muscle cells, ovarian cells, prostate cells, vaginal epithelial cells, testicular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts and osteoclasts.

In certain embodiments, more than two cell types are present in the sample. In a specific forensic embodiment, sperm cells and epithelial cells are essentially the only cell types present in the sample.

The term "cell mixture", as used herein, refers to a heterogeneous collection of at least two or more different cell types.

The term "cell suspension medium" is a buffer, or liquid, the cell mixture is present in, at the onset of analysis. The cell suspension medium can be a reconstituting buffer, if the cell mixture was originally present on a solid substrate. The reconstituting buffer can be, by way of nonlimiting example, 1× Phosphate-Buffered Saline (PBS). Cell suspension media are well-known and can be readily selected by those skilled in the art.

The term "supernatant", as used herein, describes the liquid, or buffer, present in the vessel, after cells and particles have settled to the bottom, or side, of the vessel. The supernatant can comprise impurities, such as DNA from compromised cells, or fibers from a swab, if the cell mixture was originally reconstituted from a solid substrate, or cell lysate after a lysis step has occurred, or wash buffer after a wash step has occurred. Additionally, once the cells and particles have settled to the side or bottom of a vessel, the cell suspension medium can be considered a supernatant, and can comprise impurities. In addition, a "supernatant" can describe a medium containing the lysate of one type of cell, with other cells still present in the sample.

A "vessel", for use with the present invention, can be any tube (e.g., 0.2 mL, 0.5 mL, 1 mL, 1.5 mL, 2 mL in volume), container, or well, which is open on the top, and enclosed on all sides and the bottom. Included in this definition are reagent cartridges, designed for automated equipment. Wells can be joined together to form a plate. Multiple wells can be joined together to form a plate, such as a 96-well plate or any other plate adapted to be used in automated equipment.

The term "particles responsive to a magnetic field", as used herein, is intended to encompass all particles (e.g., beads or irregular shape particles) that can capture, i.e., interact with, or associate with, cells or nucleic acid or both (under different buffer conditions). Additionally, the particles migrate when placed within the magnetic field. In some embodiments, more than one particle can associate with one another to form particle aggregates. In other embodiments, the particles are uniform in diameter and/or shape, e.g., beads. When a magnet or magnetic field is in close proximity to, or in contact with, the vessel, the particles in the reaction vessel migrate towards the source of the magnetic field. Included are ferromagnetic, paramagnetic, and superparamagnetic particles. Some non-limiting examples of commercially available particles that can be used to carry out the methods of the present invention are particles comprised of porous silica with supermagnetic core MP-50 (6.5 µm), MP-85 (>8 µm) (W. R. Grace, Columbia, Md.), iron oxide immobilized with streptavidin (Sigma, St. Louis, Mo.), and iron(III) oxide powder (5 µm) (Sigma, St. Louis, Mo.), DNA IQ™ silica particles (Promega, Madison, Wis.), MagPrep® silica particles Novagen, San Diego, Calif.), BcMag® silica-modified magnetic beads (5 µm or 1 µm) (Bioclone Inc., San Diego, Calif.), supermagnetic silica particles (1 µm or 0.75 µm, G. Kisker GbR, Steinfurt, Germany), and Dynabeads® (Invitrogen, Carlsbad, Calif.) with different type of surface functional groups (e.g., Dynabeads® MyOne carboxylic acid beads, Dynabeads® WCX, Dynabeads® TALON and Dynabeads® MyOne tosylactivated). The term "particles", as used herein, has the same meaning as "particles responsive to a magnetic field" and is simply shorthand for the longer term.

The term "short tandem repeat" (STR), as used herein, refers to all sequences between 2 and 7 nucleotides long which are tandemly reiterated within a segment of the human genome.

DNA typing (or "genotyping") involves the analysis of alleles of genomic DNA with characteristics of interest, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e. "locus") of DNA in which such a variation occurs is referred to as a "polymorphic locus."

Genetic markers which are sufficiently polymorphic with respect to length or sequence have long been sought for use in identity applications, such as paternity testing and identification of tissue samples collected for forensic analysis. The discovery and development of such markers and methods for analyzing such markers have gone through several phases of development over the last several years.

In recent years, the discovery and development of polymorphic short tandem repeats (STRs) as genetic markers has played an important role in DNA typing. In this approach, amplified alleles at each selected locus may be differentiated based on length variation. Amplification protocols with STR loci can be designed to produce small products, generally from 60 to 500 base pairs (bp) in length, and alleles from each locus are often contained within a range of less than 100 bp. This allows simultaneous electrophoretic analysis of several systems on the same gel or capillary electrophoresis by careful design of PCR primers such that all potential amplification products from an individual system do not overlap the range of alleles of other systems. These results can then be used for example to identify the parentage of human children, and to identify the source of blood, saliva, semen, and other tissue found at a crime scene or other sites requiring identification of human remains.

The term "selective sperm lysis buffer" as used herein, refers to a buffer that is capable of preferentially lysing sperm cells in a mixture comprising sperm cells and at least one other type of non-sperm cells. "Preferentially lysing sperm cells" as used herein, refers to the lysis of sperm cells, whereas nonsperm cells are not lysed. Quantitatively, at least 80%, 85%, 90%, 95%, 99% of the sperm cells are lysed, whereas at least 80%, 85%, 90%, 95% of the nonsperm cells are not lysed. In certain embodiments, only a negligible number of non-sperm cells are lysed together with the sperm cells. Nonlimiting examples of such buffers are a combination of 1M KCl and 200 mM DTT, and are also described infra.

The term "selective epithelial lysis buffer" as used herein, refers to a buffer that is capable of preferentially lysing epithelial cells in a mixture comprising sperm cells and epithelial cells. The definition is analogous to that of "selective sperm cell lysis buffer" with the quantities given above being reversed. "Preferentially lysing epithelial cells" means epithelial cells are lysed but other types of cells (e.g., sperm cells are not). In certain embodiments, a negligible amount of sperm cells (if present) are also lysed. A nonlimiting example of such a buffer is one containing 2% SDS, 20 mM EDTA, 200 mM NaCl, 20 mM Tris (pH 8) and 500 µg/mL protease K. Other buffers are within the skill of the art.

The term "wash buffer", or "washing solution", as used herein, refers to a reagent with a function of removing extraneous DNA and other impurities contained in the supernatant from cells. Washing solution can be, but is not limited to, water, PBS, Tris-HCl, or other physiologically acceptable solution. Wash buffers are commonly employed, and are known in the art.

The term "nucleic acid capture particles" can be any particles that are responsive to a magnetic field which also bind to nucleic acid present in the sample or supernatant, under specific conditions (e.g., an appropriate buffer for nucleic acid capture). The "nucleic acid capture particles" can bind DNA or RNA preferentially, or all nucleic acid. For example, nucleic acid binds to silica magnetic particles in chaotropic buffer (U.S. Pat. No. 5,234,809, incorporated in its entirety by reference). Buffers that can be employed for nucleic acid capture, with nucleic acid capture particles, can be solutions prepared from guanidium isothiocyanate (GuSCN) and guanidium chloride. Nucleic acid can also be captured by magnetic particles in solution containing high salt and alcohol (see, e.g., U.S. Pat. No. 5,523,231, U.S. Pat. No. 5,705,628, both incorporated herein, in their entirety, by reference).

The term "elution buffer", or "elution solution", as used herein, refers to a reagent with a function of disrupting or breaking the interaction of nucleic acid with nucleic acid capture particles. For example, the buffer can be any low salt solution (e.g., tris-EDTA (TE) buffer) or deionized water. Elution buffers are commonly employed, and are known in the art.

Specific Embodiments

The process of the invention can begin with resuspension of a biological specimen such as a forensic specimen in a vessel or a sample already in suspension can be provided in a vessel.

The sample contains impurities, cells and cell suspension medium. Once the sample is contained in a vessel, impurities are removed. This can be accomplished by first sequestering the cells with particles that are responsive to a magnetic field. While the vessel is in the presence of a magnetic field, the particles push the cells towards the source of the magnetic field and the cell suspension medium along with the impurities is removed, whereas the particles remain in the vessel. The removal of the cell suspension medium can be accomplished in an automated fashion or manually, by pipetting or aspirating, both gentle techniques that do not damage the cells.

In a particular forensic embodiment, a forensic specimen is reconstituted in the same vessel used for DNA isolation In another forensic embodiment, a forensic specimen is reconstituted in a different vessel, and the cell suspension is transferred to the DNA isolation vessel.

In various embodiments, a forensic sample is reconstituted in about 1 mL reconstituting buffer and gently mixed in a vessel (which may or may not be the vessel used for cell sequestration and differential extraction). The substrate is then removed from the vessel and the cells from the specimen gently centrifuged. The reconstituting buffer is then drawn off the cell pellet, and the cell pellet resuspended in 50 µL reconstituting buffer. In another embodiment, about 50 µL of the cell suspension medium is left on the cell pellet, and the cell pellet reconstituted in the original medium. Nonlimiting examples of reconstituting buffers are described infra.

In forensic embodiments such as the ones described above, a portion of the cell suspension can be used to count the number of cells originally present in the sample. The number of cells present can give the user of the method a basis for determining the quantity of particles, lysis buffers, or wash buffers, to employ. The determination as to particle quantities in particular is also a function of the size and type of particles and their mode of capturing cells and/or DNA, as one of ordinary skill in the art will readily appreciate.

In the case where a forensic specimen is reconstituted in the same vessel used for DNA isolation, the swab (e.g., cotton applicator) or other solid substrate is pushed aside (e.g., with a pipette tip or tweezers), or removed from the vessel entirely, before a magnetic field is applied. This can be accomplished either before or after particles responsive to the magnetic field are introduced into the vessel, and before or after sequestration of the cells.

Instead or in addition, cellulose digesting enzymes such as cellulase and beta-glucanase and those isolated from Fungal sources such as *Aspergillus niger, Trichoderma reesei*, and *Trichoderma viride* can be added to the reconstituting buffer or to the cell suspension in order to break down the forensic specimen's solid substrate (e.g., swab material). Although enzymes of this type can affect epitope stability on cell surface proteins, the cell membranes, and DNA content of the cells, will generally not be compromised. Nevertheless, such enzymes are also considered impurities.

In addition, some epithelial cells have their membranes compromised when a forensic specimen is taken, so extraneous epithelial DNA and other cellular components will usually be present in the initial supernatant, and removed at this step. Once the initial cell suspension medium is removed, a cell population, sequestered by the particles, remains. The removal of the supernatant can either be accomplished in an automated fashion, or manually, by pipetting or aspirating.

It should be noted that in various embodiments, present invention does not attempt to separate one intact cell type from another intact cell type. Rather, it sequesters all the intact cells together, removes the noncell extraneous material and then subjects the thus purified cell volume to selective lysis. In the sperm-epithelial cell embodiment, either sperm or epithelial cells can be lysed first. In some embodiments, selective sperm lysis is performed first. In some embodiments epithelial cell lysis is performed first and it may even precede the decanting of the initial cell suspension medium.

The sample containing cells, impurities and supernatant is placed in contact with the particles responsive to a magnetic field.

The sequestation of cells by particles responsive to a magnetic field can be achieved only if cells and particles associate during the application of a magnetic field. In some embodiments, cell and particle association is established before the application of magnetic field. In other embodiments, the association is established once the field is applied. In each case, the timing and type of association depends on the particle type and buffer conditions.

The particles responsive to a magnetic field used in the present invention can sequester the cells from the supernatant containing impurities by a number of mechanisms. In some embodiments, ionic interactions can exist between cell surfaces and the particles. In some embodiments, cell and particle association is established through antibody/antigen interaction. In some embodiments, cell and particle association is non-covalent, but the duration and strength of this association is such that it allows magnetic particles to push, drag or carry the cells to the source of the magnetic field. The type, duration and strength of this non-covalent, association between cell(s) and particle(s) is determined by the particle size, shape, surface properties, surface morphologies, particle density, solution pH and ionic strength, as those of ordinary skill readily appreciate.

Although, ionic interaction and/or hydrophobic interaction contribute to the cell/particle(s) association, cell and particle association can also be established by physical trapping or temporary attachment of particles to the cell under magnetic force if particles are smaller than cells, or physical trapping or temporary attachment of cell to particle or particle aggregates under magnetic force if cells are smaller than the particle or particle aggregates. Irregular shaped particles are more likely to form this type of cell/particle(s) association. So magnetic particles having size smaller or larger than the cells can be used to sequester the cells. Another factor that affects the efficiency of sequestration is particle density, which in turn is related to the size of the particles and the specific type of cell/particle(s) association that can be formed. In general, the particle density should be high enough that cell/particle(s) association can be established quickly during the application of magnetic force. In certain embodiments, more than one type of non-covalent interactions exist between cells and the particles and one type of interaction may be more prominent than others. Sperm cells have a diameter of about 5 μm; epithelial cells have a diameter of about 50 μm. The particles that will sequester both of these cell types will typically have a diameter within the range of 0.5-100 μm; preferably 1-10 μm with sizes outside the broader range not being excluded. The exact limits of the size range can be ascertained for a given situation of particles and cells by routine experimentation. However, the present range serves as a guide. Based on the teaching of this invention, the skilled in the art can select the appropriate particles size, shape, density and surface properties for optimal sequestering of cells in a particular application.

In some embodiments, the particles are derivatized with antibodies, particularly those intended to bind cell surface antigens that are present on all the cells in the sample so as to sequester the cells rather than attempt to separate one cell type from another. The antibodies coated particles could also be a mixture of at least two types with one type of particles coated with antibodies for epithelial cells and the other type of particles coated with antibodies for sperms cells.

Examples of epithelial and sperm cell antibodies include monoclonal BerEP4 against the human epithelial antigen, EpCAM (epithelial cell adhesion molecule); antibodies to sperm protamine; antibodies to carbohydrate epitope located on human sperm agglutination antigen-1 (SAGA-1) (see, e.g., U.S. Pat. No. 5,605,803) (incorporated by reference in its entirety); antibodies to SPAN-X, a sperm protein present in nuclear vacuoles and sperm nuclear redundant membranes (see, e.g., PCT/US99/24973) (incorporated by reference in its entirety). Other potentially useful sperm surface antigens include C58 or SMARC32 (see, e.g., U.S. Published App. 2002/0182751) (incorporated by reference in its entirety). However, epitopes present on sperm cells can be compromised in the presence of DTT and high salt, and therefore, this method may not be a method of choice in certain embodiments.

In other embodiments, the antibodies present on the particles responsive to a magnetic field are directed to ubiquitous cell surface proteins, or ubiquitous cell surface moieties (e.g., carbohydrates), present on both epithelial and sperm cells.

Other embodiments can employ particles that sequester cells based on other non-covalent interactions. Some non-covalent interactions that can be employed are hydrogen bonding, cation-π, π-π interactions, ionic pairing, hydrophobic interaction, dipole-dipole, dipole-induced-dipole, charge-dipole and van Der Waals interactions.

In some embodiments, cells are pushed, dragged or carried by the particles to the bottom of the reaction vessel, when a magnetic field is applied underneath the vessel. In some embodiments, cells are pushed, dragged or carried by the particles to the side of the reaction vessel, when a magnetic field is applied from the side of the vessel. In some embodiments, cells are pushed, dragged or carried by the particles to the magnetic bar inserted into the reaction vessel, where a magnetic bar is covered with a removable protection coat to prevent contamination. The magnetic bar can be used to transfer the particles from the vessel to another vessel.

Typically, the particles will be added in a quantity that provides an excess over the cells present in the sample. The lowest density of particles relative to that of cells in the vessel that would be needed to effect the sequestration will vary based on the mechanism of cell sequestration and the particle size and type (mode of interaction with cells) and is subject to optimization. There should be a sufficient number of particles initially present to come into contact with the cells. For example, if the particles interact with cells in a specific way, e.g., by binding cell surface epitopes with antibodies, a lower density of particles is anticipated to be required to sequester the cells than that required when the same type of particles are used but the interaction is non-specific. If sequestration occurs by particles simply pushing cells toward a magnetic field, a greater density of particles is anticipated.

In some embodiments, Dynabeads® MyOne Carboxylic Acid beads (Dynal Biotech) are used to sequester cells. The particles are 1 μm in diameter and can be typically used at a density of about $10^6$ particles/μL in a sample of about 55 cells/μL (200 μL containing about 1000 sperm cells and about 10,000 epithelial cells). Lower densities will likely still yield effective sequestration. Higher densities can naturally be used.

In some embodiments, all intact cells present in the sample are sequestered, when the vessel is placed in the presence of a magnetic field. So if the initial cell mixture is intact, substantially all cells will be sequestered. If one type of cell has already been lysed, substantially the entire remainder of intact cells will be sequestered.

In one forensic embodiment, epithelial cells are lysed with a selective epithelial lysis buffer such as one containing SDS, EDTA, Salt, Tris and protease K as illustrated infra before sequestration of the cells with particles responsive to a magnetic field. The remaining cell type(s) can then be sequestered and the epithelial cell lysate removed for downstream processing. In some embodiments, cells of a first type can be lysed before sequestration of the cells if the cell suspension medium does not contain any impurities which would contaminate the DNA of the first cell type.

The present invention can employ any commercial magnetic rack (e.g., racks supplied by Applied Biosystems, Dynal®, Invitrogen™, Promega, etc.) used for separation of beads from a liquid suspension. In some embodiments, a magnet can be used. The intensity of the magnetic field can be about 1 Tesla. In other embodiments, the strength of the field is higher than 1 Tesla. In some embodiments, the strength of the field is less than 1 Tesla.

Cell and particle sequestration occurs when a magnetic field is applied, and can take about 30 seconds. The length of time for sequestration is inversely correlated with the size of the particles and the strength of the magnetic field. Particles can be sequestered in any of the buffers used in the present invention, such as selective or general lysis buffers and wash buffers.

In some embodiments, the particles simply "push" the relatively much larger cells towards the source of the magnetic field thus sequestering them from the supernatant. The supernatant contents and other impurities are too small to be pushed along and/or do not interact with the particles, and remain behind the particles. The principle of operation of this embodiment is akin to filtration, wherein the filter (i.e., the particles) moves through the mixture to be size-separated (cells, impurities and supernatant) rather than the mixture moving through the filter. The density of the particles for this particular embodiment should be such that the spacing between particles is smaller than the size of the smallest cell in the sample.

In certain embodiments involving irregularly shaped particles and/or particle aggregates, the particle-cell interactions (and hence the sequestration efficiency) are enhanced when the irregular shaped particles or particle aggregates have interstitial spaces with a size that is comparable to the size of cells.

In certain embodiments, the sequestering of the cells could be the combined effect of more than one the above described mechanisms.

Once the cells are initially sequestered by the particles, the cell suspension medium (containing impurities) is removed from the reaction vessel. The magnetic field is discontinued (the source is turned off or the vessel is removed from the magnetic field or the source of the magnetic field is removed from the vicinity of the vessel) after sequestering the cell population and removal of the sample supernatant. Discontinuance of the magnetic field can be accomplished in an automated fashion, or manually. At this point, the cells can be washed with a wash buffer, such as 1×PBS or simply deionized water. This step serves to further reduce contaminants.

Wash steps may entail mixing the wash buffer with the particles and sequestered cells (or purified nucleic acid) by pipetting in the absence of a magnetic field. Upon completion of mixing, the magnetic field is applied, or reapplied, unless otherwise noted. Wash buffer can also be mixed by diffusion of the buffer over and through the particles (and sequestered material), in the absence of a magnetic field.

Once the cell suspension medium is removed, the first cell type is lysed. In various embodiments, selective lysis buffer is added before discontinuation of the magnetic field. In some embodiments, selective lysis buffer is added after discontinuation of the magnetic field. In various embodiments, the first cell type is sperm. One selective sperm lysis buffer that can be used in certain embodiments and is preferred is disclosed in co-pending commonly owned U.S. Provisional Application 60/899,106, incorporated by reference in its entirety.

In some embodiments, selective sperm cell lysis buffers comprise at least one disulfide bond reducing reagent (e.g., dithiothreitol (DTT), tris(2-carboxyethyl)phosphine HCl (TCEP), mercaptoethanol (ME), glutathione (GSH)) and at least one salt reagent (e.g., sodium chloride (NaCl), potassium chloride (KCl), lithium chloride (LiCl), magnesium chloride ($MgCl_2$), magnesium sulfate ($MgSO_4$), sodium nitrate ($NaNO_3$), calcium chloride ($CaCl_2$), calcium sulfate ($CaSO_4$)). Other sperm selective lysis buffers are disclosed in U.S. Published Application 2005/0032097, which is also incorporated herein by reference in its entirety.

The concentration of the salt reagent in the selective sperm lysis buffer can be at least 0.1 M. 0.5 M, 1 M, 2 M or higher. The concentration of the disulfide bond reducing reagent can be at least 0.01 M, 0.05 M, 0.1 M, 0.2 M, 0.3 M, 0.4 M, 0.5 M, 0.7 M or 0.8 M.

Based on the components taught for the selective sperm lysis buffer, one of skill in the art can easily optimize the final concentration of the salt and disulfide bond reducing reagent to lyse the sperm cells while keeping the non-sperm cells essentially intact. One nonlimiting example of selective sperm lysis buffer is a mixture of 200 mM DTT and 1 M KCl.

In various embodiments of the invention, mixing the selective sperm lysis buffer with the sequestered cells can be accomplished by pipetting up and down into the vessel. In some embodiments, the selective lysis buffer and cell population are combined and vortexed at a low speed, in order to allow for full interaction between cells and lysis buffer. In some embodiments, the cells are lysed by diffusion. Lysis buffer conditions and type of mixing employed influence the duration of the lysis step. These conditions can be optimized using no more than ordinary skill and optimization is dependent on the particular application (e.g., forensic or not, types of cells involved etc.) of the present methods.

In certain embodiments, the components of the selective sperm lysis buffer are added sequentially with the sequestered cells and mixed one-by-one with the cells. Alternatively, mixing does not occur until both components (i.e., the salt and disulfide bond reducing agent) are added. In some embodiments, the disulfide bond reducing agent is added first. In some embodiments, lysis occurs by diffusion and, therefore, mixing is not performed by the user. In various embodiments, mixing occurs by a combination of passive mixing and active mixing (e.g., by vortexing or pipetting).

In various embodiments, incubation with selective sperm lysis buffer is carried out at any temperature for a length of time sufficient to achieve the appropriate results. In certain embodiments, the incubation is carried out at room temperature. Alternatively, the incubation can be carried out at approximately 20-50° C. The incubation interval ranges from about 1 minute to 4 hours or longer, with more specific typical intervals being 5 minutes or 10 minutes.

In some embodiments, the lysate of the first cell type is sperm cell lysate. It can be recovered from the reaction vessel by reapplying a magnetic field to the reaction vessel, thereby sequestering the cells that were not lysed. The supernatant, after selective lysis, will include the sperm cell lysate, and can be subsequently removed from the vessel. This can be accomplished in an automated fashion, or manually by pipetting. An optional wash can be performed at this stage to further reduce any first lysate DNA that would contaminate the intact cells of the second type. Alternatively, lysis can occur before cell sequestration and the cell suspension medium is discarded. In particular embodiments wherein sperm DNA needs to be separated from epithelial cell DNA, epithelial cells may optionally be lysed first, before sequestration. The cell suspension medium will then contain the epithelial cell lysate. The remaining intact cells (essentially only sperm cells) can then be sequestered and the medium containing the epithelial cell lysate removed for further purification of the DNA contained therein. The sperm cells can then be lysed as described elsewhere herein.

The lysate of the first type of cells can then be used in downstream assays to determine nucleic acid content or identity.

In some embodiments, the DNA, mRNA, or total RNA is purified from the lysate, in preparation for a downstream application, such as amplification, sequencing or STR analysis, all of which are known analytical methods. Purification can be employed in any vessel or predispensed reagent cartridge. Purification can entail mixing the lysate with nucleic acid capture particles and an appropriate buffer for nucleic acid, or in a various embodiments, DNA capture. Nonlimiting examples of particles that can be used are those described earlier herein.

In the embodiment where the lysate of the first cell type is purified with particles, an elution buffer is used to concentrate the nucleic acid in solution, and out of the solid state. Nonlimiting examples of elution buffers include deionized water, TE buffer, and any other low-salt buffer. In addition, heat may be added to the elution reaction during this step.

In some embodiments, the lysate can be used for downstream reactions (e.g., nucleic acid amplification or sequencing), without further purification.

In certain embodiments, the methods of the present invention further comprise isolation and recovery of a second cell type's nucleic acid, after removal of the first cell type's lysate. In some embodiments, the original sample contains two cell types and lysis of the second cell type need not be selective. Instead, it can be carried out, for example, with any chaotropic, high salt, or detergent based lysis buffer. In various embodiments, lysis can be carried out by subjecting the cells to heat, in order to break open the cells. Isolation and analysis of the second cell type (e.g., epithelial cells) in addition to the sperm cells permits assailant and victim to be both identified and associated.

In various embodiments, there are more than two cell types in the sample and lysis of the second cell type is preferably carried out selectively. It will become clear to one of skill in the art, once the cell types are known, as to what type of selective lysis buffer to employ. In some embodiments, the second cell type is epithelial and can be lysed selectively with a buffer, for example one containing 2% SDS, 20 mM EDTA, 200 mM NaCl, 20 mM Tris (pH 8) and 500 μg/mL protease K.

In various embodiments of the invention, and in order to lyse a second specific cell type, the selective lysis buffer, or a general lysis buffer (depending on the contents of the original sample and the specific purpose of nucleic acid recovery) is mixed with the sequestered cells by pipetting up and down into the vessel.

In some embodiments, the second lysis buffer and cell population are vortexed, in order to allow for full interaction between cells and lysis buffer. In some embodiments, the cells are lysed passively by diffusion without vortexing or mixing. Lysis buffer conditions and type of mixing employed dictate how long the lysis step is carried out for. These conditions can be optimized and are dependent on the particular application.

The magnetic field is discontinued again after removing the first cell type's lysate. In various embodiments, a second selective or a nonselective lysis buffer is added before discontinuation of the field. In some embodiments, lysis buffer is added after discontinuation of the field. The lysis buffer, for lysis of the second cell type, is added only after removal of the first cell type's lysate and any optional wash steps.

The particles for cell trapping could also be used for DNA purification under appropriate conditions. For example, when magnetic silica particles are used to trap cells, the trapped cells can be lysed and the released DNA can be captured and purified by the same trapping particles based on standard silica/chaotropic chemistry (e.g., U.S. Pat. No. 5,234,809 incorporated by reference in its entirety). In another example, if Dynabeads® MyOne carboxylic acid beads or magnetic iron oxide particles are used for cell trapping, DNA precipitation chemistry can be used to purify DNA after cell lysis (see, e.g., U.S. Pat. No. 5,523,231, U.S. Pat. No. 5,705,628 both incorporated in their entirety by reference).

In some embodiments, the lysate of the second cell type is purified in another vessel, or specifically a compartment of a predispensed reagent cartridge, with magnetic particles and an appropriate buffer (suitable for binding of nucleic acid to particles). This step is accomplished in a similar fashion to the embodiment describing the isolation of the nucleic acid of the first cell type.

Once the nucleic acid has been captured on the nucleic acid capture particles, optional wash steps can be employed using a wash buffer, e.g., 70% ethanol. Wash steps are carried out in the same manner as described above.

In the embodiment where the lysate of the second cell type is purified with particles, an elution buffer is used to concentrate the nucleic acid in solution, and out of the solid state. Exemplary elution buffers include deionized water, TE buffer, and any other low-salt buffer. In addition, heat may be added to the elution reaction during this step.

If only two cell types are present initially in the sample, the second cell lysate can be manipulated in the original reaction vessel for downstream applications. In addition, if only the nucleic acid of the first type is to be analyzed, the nucelic acid can be further isolated from the lysate, by removing the lysate and purifying in another vessel. The purification step can entail the use of particles responsive to a magnetic field, and an appropriate buffer, such as one containing guanidium or on the particles responsive to a magnetic field, by changing buffer and/or reaction conditions.

The nucleic acid (either DNA or RNA, preferably DNA) can be isolated further from the lysate using the same particles originally used to sequester the cell populations. DNA is purified by the particles in the original vessel by changing the buffer conditions depending on the types of magnetic particles used for sequestering (e.g., by adding heat, salt, increasing or decreasing pH, etc.) in the vessel. For example, if the sequestering particles are magnetic silica particles, DNA is captured by the particles in the original vessel by adding 5M GuSCN solution to the vessel. DNA on the particles is then washed with ethanol. Elution of the nucleic acid can then be carried out as described above.

In some embodiments, the second cell lysate is also removed from the vessel, either in an automated fashion, or manually, as described supra. If other cells (e.g., of a third type) are still present in the vessel, the magnetic field is reapplied to the vessel, in order to sequester the remaining cells, and the lysate is removed for further manipulation. The lysate can then be introduced into downstream assays, for example, nucleic acid purification, amplification, sequencing or STR typing.

In the embodiment where more than two cell types are present, additional general lysis or selective lysis can be carried out on the remaining cells, after lysis and removal of first and second lysate as described for the previous cell types. In addition, removal of the additional lysates, and sequestration of the remaining cells can be carried out as described for the first and second cell types.

FIG. 1 shows steps that can be taken, in a particular embodiment of the invention, to isolate nucleic acid from a specific cell type in a sample containing a heterogenous population of cells. A specimen containing cells and impurities, e.g., comprising a forensic specimen, for example a vaginal swab, is provided at step 310. The specimen can be reconstituted in the reaction vessel, or in another vessel, at step 320. The swab itself can be removed e.g., pushed aside, or it (or swab debris left after removal of the swab) can be digested using cellulose digesting enzymes. The sample, at step 330, is combined in the reaction vessel with particles that are responsive to a magnetic field. A magnetic field is applied to the vessel at step 340, thereby causing sequestration of the cells in the sample by the particles. Once the cells are sequestered, the cell suspension medium (containing impurities and epithelial cell DNA) is removed from the reaction vessel. This is shown as step 350. At step 360, a selective lysis buffer is introduced into the vessel and cells of the first type, preferably sperm cells, are selectively lysed, at step 370. The nucleic acid of the first cell type is isolated and recovered at step 380, for further nucleic acid purification, and/or downstream identification assays, such as sequencing or STR analysis.

In certain embodiments of the invention, wash steps can be employed with a wash buffer, after removal of lysate, and prior to lysing the next cell type. The wash steps are carried out to remove or further reduce remaining impurities that may associate with the sequestered particles, but are not necessary steps of the methods of the invention. Addition and removal of wash buffer can be accomplished either manually, by pipetting, or in an automated fashion. Optional wash steps can be performed, with specific reference to FIG. 1, between steps 350 and 360.

In a various embodiments of the present invention, selective lysis of the first cell type at step 370, is carried out by discontinuing the application of the magnetic field followed by mixing a selective lysis buffer with the particles and cells present in the sample.

In certain embodiments, the nucleic acid of the first cell type is isolated and recovered at step 380 by reapplying the magnetic field to the vessel, thereby sequestering the remaining cells followed by removing lysate of the first cell type from the reaction vessel.

In some embodiments of the invention, a second cell type is lysed and its nucleic acid isolated and recovered, after removal of the first cell lysate from the vessel. This can be accomplished by discontinuing application of the magnetic field from the vessel, introducing a lysis buffer to the vessel, lysing the second cell type use either a selective or general lysis buffer, and isolating the nucleic acid of the second cell type.

If other cells types still remain in the vessel, after lysis of the second cell type, the nucleic acid of the second cell type is isolated and recovered by reapplying the magnetic field to the vessel, thereby sequestering the remaining cells followed by removing lysate of the second cell type from the reaction vessel. If no cells remain in the vessel, reapplication of the magnetic field is not necessary, and downstream assays may be carried out in the same vessel (note, however, that the magnetic field may be reapplied to capture DNA from cell lysate). Alternatively, the lysate of the second cell type is removed from the vessel for use in downstream assays, or purification protocols.

In various embodiments, the components to carry out selective lysis of a cell type, and recovery of its nucleic acid, in a sample containing more than one cell type, are supplied as a kit. A specific kit includes at least one reaction vessel, a quantity of particles responsive to a magnetic field, predetermined to be sufficient to sequester cells in a sample containing a specific quantity of cells, a quantity of selective lysis buffer sufficient to lyse the cells of the first type, a quantity of a general or selective lysis buffer, sufficient to lyse cells of the second cell type, a wash buffer, and instructions for use. The present method can be practiced with existing instrumentation which provides a source of a magnetic field. Sequestration of cells can be discerned visually.

The present invention is further illustrated by reference to the Examples below. However, it should be noted that these Examples, like the embodiments described above, are illustrative and are not to be construed as restricting the enabled scope of the invention in any way.

Example 1

Sperm Cell and Epithelial Cell DNAs Isolation and Analysis

A mock forensic sample was prepared as follows: Three month old female buccal swab was reconstituted into 1 mL 1×PBS buffer to provide epithelial cells. 5 µL (1,000 cells per microliter) of a sperm cell suspension were then added to 155 µL of the epithelial cell suspension. The resulting mock forensic sample contained sperm cells, epithelial cells and extraneous epithelial DNA. At this point the number of epithelial cells in the mock sample was unknown.

40 µL of trapping magnetic particles (Dynabeads MyOne Carboxylic Acid, Dynal Biotech) were added to the vessel, containing the heterogeneous cell sample. The contents of the vessel were then mixed by pipetting up and down.

Cells were then sequestered by putting the sample on 6 Tube Magentic stand (herein "MagRack", Applied Biosystems, Foster City, Calif.). Once the cells were sequestered, the supernatant, containing extraneous DNA, was removed from the vessel by pipetting. The vessel was then taken off the MagRack and 200 µL sperminator lysis buffer was added to the vessel to selectively lyse sperm cells. The cells and buffer were mixed at the beginning and end of a 5 minute incubation at room temperature by pipetting up and down a few times.

Upon completion of lysis, the vessel was placed on the MagRack for about 30 seconds to trap the remaining epithelial cells, still in solution. Once the particles were sequestered at the side of the vessel (because the magnetic field, i.e., MagRack, is placed on the side of the vessel), the sperm cell lysate was recovered from the vessel and placed in another vessel for subsequent STR typing.

The epithelial cells, still sequestered by the particles, were then washed with 200 µL of wash buffer (1×PBS, pH 7.4). The wash was accomplished by pipetting the PBS up and down on the sequestered beads and particles. The vessel was then taken off the MagRack and 100 µL epithelial cell lysis buffer (5M GuSCN) was added to the vessel. The content of the vessel was mixed by pipetting before the vessel was placed in a 70° C. heat block for 5 minutes to lysis the epithelial cells. Upon completion of lysis, the vessel was placed back on the MagRack and the epithelial cell lysate was recovered by pipetting, and placed in another vessel for downstream STR typing.

Next, DNA purification was carried out using Applied Biosystems's proprietary DNA purification method. DNA can also be purified using commercially available kits such as DNA IQ™ from Promega. After DNA purification, the sperm DNA was quantified using the Quantifiler® Human Male DNA Quantification Kit (Applied Biosystems, Foster City, Calif.) and the epithelial DNA is quantified using the Quantifiler® Human DNA Quantification Kit (Applied Biosystems, Foster City, Calif.).

Approximately 1 ng of sperm or epithelial DNA was used for each amplification reaction. STR amplification was carried out using AmpFlSTR® Indenfiler® PCR Amplification Kit (Applied Biosystems, Foster City, Calif.) on a GeneAmp® PCT System 9700 (Applied Biosystems, Foster City, Calif.) according to the manufacturer's protocol.

STR typing was carried out using ABI PRISM 3100 Genetic Analyzer and data was analyzed using GenMapID3.2.

Results of sperm cell analyses are given in FIGS. 2A-2D, along with STR typing of control samples of sperm DNA (FIGS. 2E-2H). As can be seen in these Figures, resolution of sperm DNA is complete even though the sperm cell to epithelial cell ratio was only 1:48. In addition, thirteen of the fifteen loci analyzed are the required loci for the combined DNA Index System (CODIS) for known-offender databasing in the United States. The fifteen loci analyzed are consistent with several worldwide database recommendations.

Epithelial STR typing results are given in FIG. 3A-3D, along with epithelial DNA Again, resolution is complete for all 15 loci analyzed.

Example 2

Selectively Lysing Sperm Cells Which are Present in a Heterogeneous Cell Suspension Two samples were made, each containing about 100,000 sperm cells and 100,000 epithelial cells in 60 μL 1×PBS. 140 μL of 1×PBS and 1 μL of propidium iodide (1 mg/mL) were added to the first sample.

100 μL of 2M KCl, 40 μL of 1M DTT and 1 μL of propidium iodide (1 mg/mL) were added to the second sample. The final concentrations in the 200 μL second sample were 1M KCl an d200 mM DTT. The samples were then mixed and incubated at room temperature for 5 min. Both samples were examined under fluorescent microscopes.

Figure 4A:
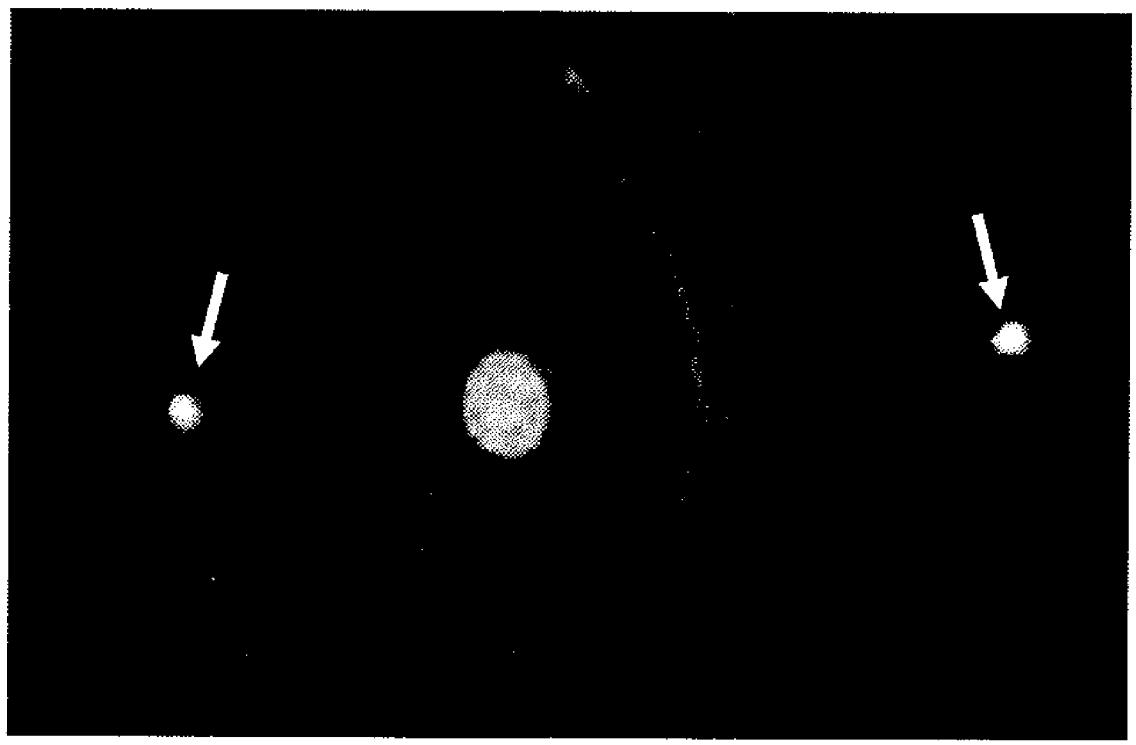
FIG. 4A is a fluorescent image of intact epithelial cells and sperm cells (arrows) in sample 1 of Example 3.
Figure 4B:
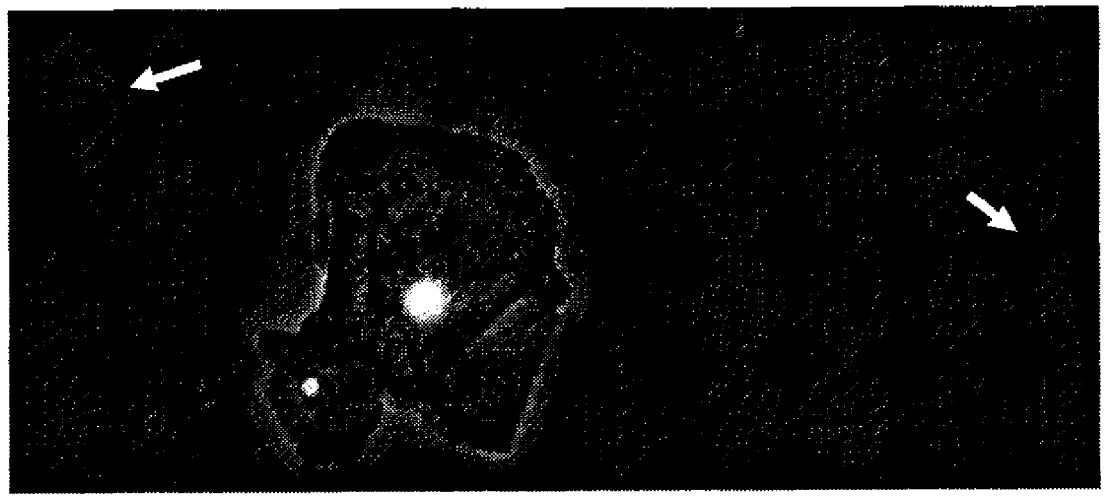
FIG. 4B is a fluorescent image of epithelial cells and sperm cells after selective sperm lysis in sample 2 of Example 3. Sperm cells were completely lysed and only sperm tails (arrows) were visible, while epithelial cells are still intact.

FIG. 4A is the image of the cells from sample 1. FIG. 4B is the image of the cells from sample 2. Both panels of the figure show that the epithelial cells remained intact in both the first and second sample. The sperm cells, in contrast, were lysed in the second sample, but not in the first sample. The, the presence of KCl and DTT in the second sample, resulted in selective lysis of the sperm cells.

Although the invention has been described in terms of exemplary embodiments, it is not limited thereto. The claims should be construed broadly to include other embodiments of the invention that can be made by ones of ordinary skill in the art.

The invention is further described below by reference to claims as follows:

I claim:

1. A method for selectively recovering nucleic acid from a first cell type in a sample containing intact cells of at least a first cell type and a second cell type, and a cell suspension medium comprising extracellular impurities, said impurities optionally including contaminating DNA, the method comprising:
combining said sample with particles responsive to a magnetic field in a vessel, said magnetic particles having the ability to sequester the intact cells from said cell suspension medium upon application of a magnetic field;
applying a magnetic field to the vessel, thereby causing sequestration of said intact cells by said particles;
removing the impurities-containing cell suspension medium from the vessel while retaining said intact cells;
lysing selectively intact cells of the first cell type in the presence of intact cells of the second cell type; and
isolating the nucleic acid from the lysed cells.

2. The method of claim 1 further comprising a particle and cell wash step prior to the lysing step.

3. The method of claim 1 wherein the step of lysing selectively the first cell type comprises:
discontinuing application of the magnetic field; and
exposing the sequestered cells to a selective lysis buffer for a time sufficient to lyse the cells of the first type.

4. The method of claim 3 wherein the isolating step comprises:
re-applying the magnetic field to the vessel, thereby sequestering the remaining cells, including cells of the second type; and
recovering the lysate containing said nucleic acid from the first cell type.

5. The method of claim 1 wherein recovering the nucleic acid from the first cell type comprises removing the lysate containing the nucleic acid of the first cell type from the reaction vessel.

6. The method of claim 1, further comprising recovering nucleic acid of the second cell type.

7. The method of claim 6, wherein recovering nucleic acid from the second cell type comprises:
discontinuing application of the magnetic field from the vessel;
lysing the second cell type using a lysis buffer; and
isolating the nucleic acid from the lysate of the second cell type.

8. The method of claim 7 further comprising a particle wash step prior to discontinuing application of the magnetic field from the vessel.

9. The method of claim 7 wherein lysing the second cell type is accomplished using a selective lysis buffer.

10. The method of claim 7 wherein the isolating step comprises capturing the lysed nucleic acid from cells of the second type with said particles.

11. The method of claim 1 wherein the nucleic acid is DNA.

12. The method of claim 1 wherein the nucleic acid is RNA.

13. The method of claim 1 wherein the first cell type is sperm.

14. The method of claim 13 wherein the second cell type is epithelial.

15. The method of claim 1 comprising purifying the recovered nucleic acid to a purity sufficient for sperm STR profiles to be obtained that are useful in genotyping.

16. A method of recovering nucleic acid according to claim 1 further comprising amplifying and sequencing at least a predetermined region of said nucleic acid after isolation of said nucleic acid.

17. A method for identifying a nucleic acid from a first cell type in a sample containing intact cells of at least a first and a second cell type, and a supernatant comprising extracellular impurities, said impurities optionally including contaminating DNA, the method comprising:

combining said sample with particles responsive to a magnetic field in a vessel, said magnetic particles having the ability to sequester said intact cells from said supernatant upon application of a magnetic field;

applying a magnetic field to the vessel, thereby causing sequestration of said intact cells by said particles;

removing the impurities-containing supernatant from the vessel while retaining said intact cells;

lysing selectively intact cells of the first cell type in the presence of intact cells of the second cell type; and isolating the nucleic acid from the lysed cells and amplifying a predetermined region of said nucleic acid.

18. The method of claim 17 wherein the predetermined region of said nucleic acid is comprised of short tandem repeats having from 2 to 7 nucleotides.

19. A kit for the selective isolation of nucleic acid from a first cell type in a sample containing cells of at least a first and a second cell type, and a supernatant comprising extracellular impurities, the kit comprising:

a quantity of particles responsive to a magnetic field capable of sequestering at least the first cell type and at least the second cell type in the sample, at least one reaction vessel, a selective lysis buffer for the first cell type, a lysis buffer for the second cell type and optionally an instruction manual for isolating said nucleic acid.

20. A method for selectively recovering nucleic acid from a first cell type in a sample containing (i) intact cells of at least a first and a second cell type, (ii) cell suspension medium comprising extracellular impurities, said impurities optionally including contaminating nucleic acid of the same cell type as said first cell type, and (iii) magnetic particles, said magnetic particles having the ability to sequester said intact cells from said medium upon application of a magnetic field, the method comprising:

lysing selectively intact cells of the first cell type in the presence of intact cells of the second cell type;

applying a magnetic field to a vessel containing said lysate, said medium and intact cells of the second type, thereby causing sequestration of said intact cells of said second type by said particles; removing said lysate and said medium; and isolating nucleic acid from said lysate and medium.

21. A method for selectively recovering nucleic acid from a first cell type in a sample containing (i) intact cells of at least a first and a second cell type, (ii) a cell suspension medium comprising extracellular impurities, said impurities optionally including contaminating nucleic acid, and (iii) magnetic particles, said magnetic particles having the ability to sequester said intact cells from said medium upon application of a magnetic field, the method comprising:

applying a magnetic field to a vessel containing said sample, thereby causing sequestration of said intact cells by said particles;

removing the impurities-containing supernatant from the vessel while retaining said intact cells;

lysing selectively intact cells of the first cell type in the presence of intact cells of the second cell type; and isolating the DNA from the lysed cells.

22. A method for selectively isolating nucleic acid from a first cell type in a sample containing intact cells of at least a first cell type and a second cell type, and a cell suspension medium comprising extracellular impurities, said impurities optionally including contaminating DNA, the method comprising:

providing a forensic specimen containing a heterogeneous population of intact cells;

reconstituting said specimen to form a sample;

combining said sample with particles responsive to a magnetic field;

applying a magnetic field to a vessel containing said sample, thereby causing sequestration of said intact cells by said particles;

removing the impurities-containing cell suspension medium from the vessel while retaining said intact cells;

introducing a lysis buffer selective for the first cell type to said vessel;

lysing selectively intact cells of the first cell type in the presence of intact cells of the second cell type; and isolating nucleic acid from the lysed cells.

* * * * *